US011061150B2

(12) United States Patent
Ye

(10) Patent No.: US 11,061,150 B2
(45) Date of Patent: Jul. 13, 2021

(54) CT DETECTOR MODULE AND HEAT DISSIPATION STRUCTURE

(71) Applicant: SHANGHAI UNITED IMAGING HEALTHCARE CO., LTD., Shanghai (CN)

(72) Inventor: Ting Ye, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 905 days.

(21) Appl. No.: 15/721,780

(22) Filed: Sep. 30, 2017

(65) Prior Publication Data
US 2019/0072679 A1    Mar. 7, 2019

Related U.S. Application Data

(63) Continuation of application No. PCT/CN2017/100659, filed on Sep. 6, 2017.

(51) Int. Cl.
*A61B 6/00* (2006.01)
*G01T 1/24* (2006.01)
*G01T 1/29* (2006.01)
*A61B 6/03* (2006.01)

(52) U.S. Cl.
CPC ............... *G01T 1/244* (2013.01); *A61B 6/03* (2013.01); *A61B 6/032* (2013.01); *A61B 6/4266* (2013.01); *A61B 6/4291* (2013.01); *G01T 1/2985* (2013.01)

(58) Field of Classification Search
CPC ..... G01T 1/244; G01T 1/2985; G01T 1/2006; A61B 6/4291; A61B 6/032; A61B 6/4266; A61B 6/03; G02B 5/00; G02B 5/003
See application file for complete search history.

(56) References Cited

U.S. PATENT DOCUMENTS

| 2012/0069956 | A1  | 3/2012 | Guery et al. |
| 2013/0221228 | A1* | 8/2013 | Kuroda ................. G01T 1/2018 250/366 |
| 2015/0156920 | A1  | 6/2015 | Kawaguchi et al. |
| 2016/0170038 | A1  | 6/2016 | Yu |
| 2017/0213612 | A1* | 7/2017 | Ikhlef ................... G01T 1/2018 |

FOREIGN PATENT DOCUMENTS

| CN | 103181771 A | 7/2013 |
| CN | 103549972 A | 2/2014 |

OTHER PUBLICATIONS

International Search Report in PCT/CN2017/100659 dated May 30, 2018, 5 pages.
Written Opinion in PCT/CN2017/100659 dated May 30, 2018, 4 pages.

* cited by examiner

*Primary Examiner* — David P Porta
*Assistant Examiner* — Mamadou Faye
(74) *Attorney, Agent, or Firm* — Metis IP LLC

(57) ABSTRACT

A detector module is provided. The detector module may include a plurality of detector sub-modules. Each of the plurality of detector sub-modules may include a detection layer, at least one data acquisition circuitry, a frame for supporting the detection layer, and a positioning element for assembling the plurality of detector sub-modules. The frame may include a plurality of heat transfer fins that are thermally connected with the at least one data acquisition circuitry for dissipating heat produced by the at least one data acquisition circuitry.

19 Claims, 14 Drawing Sheets

700

1100

CT DETECTOR MODULE AND HEAT DISSIPATION STRUCTURE

CROSS-REFERENCE TO RELATED APPLICATIONS

The application is a continuation of International Application No. PCT/CN2017/100659, filed on Sep. 6, 2017, the contents of which are incorporated herein by reference.

TECHNICAL FIELD

The present disclosure generally relates to an imaging apparatus, and more particularly, to a CT detector module with a heat dissipation structure.

BACKGROUND

A detector module in a computed tomography (CT) device may be used for receiving radiation emitted by a CT tube and converting the radiation into digital signals for image processing. The detector module may include a photodetector, a data acquisition circuitry, a scintillator, etc. During operation, an analog-to-digital converter (ADC) on the data acquisition circuitry may produce considerable heat, which may interfere with the performance of the photodetector, the scintillator, etc. Accordingly, it would be desirable to provide a heat dissipation structure to reduce the heat produced by the detector module.

SUMMARY

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

According to an aspect of the present disclosure, a detector module is provided. The detector module may include a plurality of detector sub-modules. The plurality of detector sub-modules may include a first detector sub-module and a second detector sub-module adjacent to the first detector sub-module. The plurality of detector sub-modules may be detachably assembled. The first detector sub-module may include a first positioning element, and the second detector sub-module may include a second positioning element. Each of the plurality of detector sub-modules may include a detection layer to detect radiation and at least one data acquisition circuitry that is electrically connected with the detection layer. The at least one data acquisition circuitry may be configured to process an electrical signal in response to the radiation detected by the detection layer. A detector sub-module may further include a frame that supports the detection layer and the at least one data acquisition circuitry. The first positioning element and the second positioning element may form a mating connection.

In some embodiments, the first positioning element of the first detector sub-module may include a boss disposed on a first side of the detector sub-module. The second positioning element of the second detector sub-module may include a recessed pocket disposed on a second side of the second detector sub-module. The second side of the second detector sub-module may be situated to face the first side of the first detector sub-module.

In some embodiments, the plurality of detector sub-modules may be assembled based on a bolt inserted through the boss and the recessed pocket.

In some embodiments, a detector sub-module of the plurality of detector sub-modules may further include a plurality of fins that may be thermally connected with the at least one data acquisition circuitry of the detector sub-module.

In some embodiments, the plurality of fins of the detector sub-module may be disposed on a third side of the frame. The data acquisition circuitry may be disposed on a fourth side of the frame. The fourth side may be opposite to the third side.

In some embodiments, the at least one data acquisition circuitry may be electrically connected with two signal transmission boards disposed on opposite sides of the frame. The two signal transmission boards may be electrically connected to the detection layer of the detector sub-module.

In some embodiments, the at least one data acquisition circuitry may be electrically connected with a signal transmission board that may be disposed on a same side of the frame as the at least one data acquisition circuitry.

In some embodiments, the plurality of fins may be disposed on opposite sides of the frame.

In some embodiments, the detector sub-module may include two data acquisition circuitries that may be disposed on opposite sides of the frame of the detector sub-module.

In some embodiments, the detector sub-module may include two signal transmission boards that may be disposed on opposite sides of the frame. Each of the two signal transmission boards may be electrically connected with one of the two data acquisition circuitries.

In some embodiments, the frame may be configured to support an anti-scatter grid that may be disposed on a top of the detection layer.

According to another aspect of the present disclosure, a detector module is provided. The detector module may include a frame and a detection layer supported by the frame. The detection layer may be configured to detect radiation. The detector module may further include at least one data acquisition circuitry that is electrically connected with the detection layer. The at least one data acquisition circuitry may be configured to process an electrical signal in response to the radiation detected by the detection layer. The detector module may further include a dissipation structure which includes a plurality of fins that may be thermally coupled with the at least one data acquisition circuitry.

In some embodiments, the plurality of fins may be disposed on a first side of the frame. The at least one data acquisition circuitry may be disposed on a second side of the frame. The first side may be opposite to the second side.

In some embodiments, the at least one data acquisition circuitry may be electrically connected with a first signal transmission board that may be disposed on a same side of the frame as the at least one data acquisition circuitry. The first signal transmission board may be electrically connected to the detection layer of the detector module.

In some embodiments, the at least one data acquisition circuitry may be electrically connected with a second signal transmission board that may be disposed on a same side of the frame as the plurality of fins. The second signal transmission board may be electrically connected to the detection layer of the detector module.

In some embodiments, a first portion of the plurality of fins may be disposed on a third side of the frame. A second portion of the plurality of fins may be disposed on a fourth side of the frame. The third side may be opposite to the fourth side.

In some embodiments, the at least one data acquisition circuitry may be disposed on the third side or the fourth side of the frame.

In some embodiments, the at least one data acquisition circuitry may include a first data acquisition circuitry and a second data acquisition circuitry. The first data acquisition circuitry may be disposed on the third side of the frame. The second data acquisition circuitry may be disposed on the fourth side of the frame.

In some embodiments, the first data acquisition circuitry may be electrically connected with a third signal transmission board disposed on a same side of the frame as the first data acquisition circuitry. The second data acquisition circuitry may be electrically connected with a fourth signal transmission board that may be disposed on a same side of the frame as the second data acquisition circuitry.

In some embodiments, the detector module may further include a recessed pocket disposed on the frame. The recessed pocket may be configured to receive a boss of another detector module to assemble the detector module and the other detector module.

BRIEF DESCRIPTION OF THE DRAWINGS

The present disclosure is further described in terms of exemplary embodiments. These exemplary embodiments are described in detail with reference to the drawings. These embodiments are non-limiting examples, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirits and scope of the present disclosure. Thus, the present disclosure is not limited to the embodiments shown, but to be accorded the widest scope consistent with the claims.

It will be understood that the term "system," "unit," "module," and/or "block" used herein are one method to distinguish different components, elements, parts, section or assembly of different level in ascending order. However, the terms may be displaced by another expression if they may achieve the same purpose.

It will be understood that when a unit, module or block is referred to as being "on," "connected to" or "coupled to" another unit, module, or block, it may be directly on, connected or coupled to the other unit, module, or block, or intervening unit, module, or block may be present, unless the context clearly indicates otherwise. As used herein, the term "and/or" includes any and all combinations of one or more of the associated listed items.

The terminology used herein is for the purposes of describing particular examples and embodiments only, and is not intended to be limiting. As used herein, the singular forms "a," "an," and "the" may be intended to include the plural forms as well, unless the context clearly indicates otherwise. It will be further understood that the terms "include," and/or "comprise," when used in this disclosure, specify the presence of integers, devices, behaviors, stated features, steps, elements, operations, and/or components, but do not exclude the presence or addition of one or more other integers, devices, behaviors, features, steps, elements, operations, components, and/or groups thereof.

Figure 1:
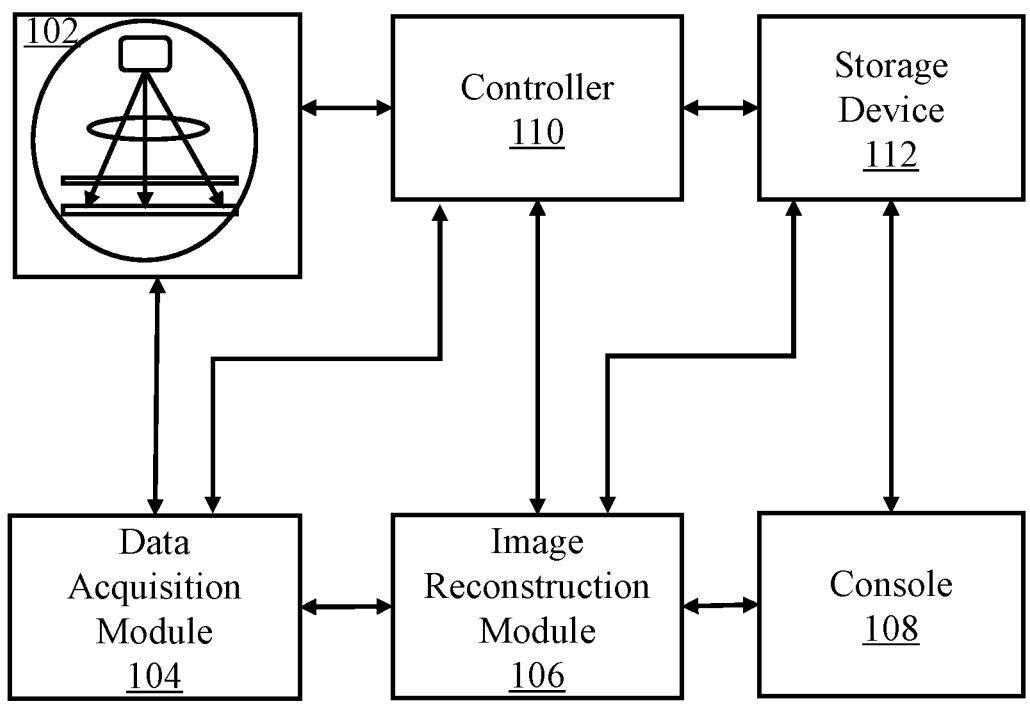
FIG. 1 is a schematic block diagram of an exemplary imaging system according to some embodiments of the present disclosure.

FIG. 1 is a schematic block diagram of an exemplary imaging system 100 according to some embodiments of the present disclosure. As shown, the imaging system 100 may include an imaging apparatus 102, a data acquisition module 104, an image reconstruction module 106, a console 108, a controller 110, and a storage device 112. It should be noted that the imaging system described below is merely provided for illustration purposes, and not intended to limit the scope of the present disclosure. The imaging system 100 may find its applications in various fields, such as healthcare industries (e.g., medical applications), security applications, industrial applications, etc. For example, the imaging system 100 may be used for internal inspections of components including, e.g., flaw detection, security scanning, failure analysis, metrology, assembly analysis, void analysis, wall thickness analysis, or the like, or a combination thereof. The imaging system may be a computed tomography (CT) system, a digital radiography (DR) system, a computed radiography (CR) scanner, a multi-modality system, or the like, or a combination thereof.

The imaging apparatus 102 may be a computed tomography (CT) scanner, a digital radiography (DR) scanner, a computed radiography (CR) scanner, a multi-modality imaging device, or the like, or a combination thereof. Exemplary multi-modality imaging devices may include a computed tomography-positron emission tomography (CT-PET) scanner, a computed tomography-magnetic resonance imaging (CT-MRI) scanner, etc. The imaging apparatus 102 may generate a signal by scanning an object with radiation beams. The radiation beams may include a photon ray. The photon ray may include an X-ray, a γ-ray, ultraviolet, laser, or the like, or a combination thereof. The object may include a substance, a tissue, an organ, a specimen, a body, a human being, or the like, or a combination thereof. The signal may be an optical signal such as a visible light signal containing characteristic information of the object, such as density, thickness, composition, etc. In some embodiments, a detector in the imaging apparatus 102 may detect a radiation beam traversing an object to generate a signal. For example, the detected radiation beam may excite a scintillating material on the detector to generate a visible light signal.

The data acquisition module 104 may obtain a signal generated by the imaging apparatus 102. For example, the data acquisition module 104 may receive a light signal from the imaging apparatus 102. The light signal may be generated by radiation beams from the imaging apparatus 102. At least a portion of the radiation beams may have traversed the object before being detected. The data acquisition module 104 may include an optoelectronic conversion unit, an analog-digital converter (ADC), or the like, or a combination thereof. The optoelectronic conversion unit may convert the light signal into an electronic signal. The analog-digital converter may convert the electronic signal into a digital signal, such as a digital signal encoding projection data. The projection data may be transmitted to the image reconstruction module 106. It should be noted that, in some embodiments, the optoelectronic conversion unit and/or the analog-digital converter may be unnecessary, or may be integrated into the imaging apparatus 102.

The image reconstruction module 106 may generate an image based on data relating to an object obtained from the data acquisition module 104, or the storage device 112. The data relating to the object may include projection data corresponding to radiation beams traversing the object. The image may be generated using a suitable analytical, an iterative, and/or other reconstruction techniques. The image reconstruction module 106 may be connected to or communicate with the data acquisition 104, the console 108, the controller 110, and the storage 112 via a wireless connection, a wired connection, or a combination thereof.

The console 108 may be a user interface through which a user or an operator may communicate with different components in the imaging system 100. The console 108 may include an input device, a control panel, etc. The input device may include alphanumeric and other keys that may be input via a keyboard, a touch screen (for example, with a haptics or tactile feedback), a speech input, an eye tracking input, a brain monitoring system, or any other comparable input mechanism. The input device may also include, for example, a cursor control device, such as a mouse, a trackball, or cursor direction keys, etc. The console 108 may display images generated by the image reconstruction module 106. The console 108 may send a command or an instruction from a user or an operator to the image reconstruction module 106, and/or the controller 110. The console 108 may set one or more parameters for the imaging system 100, including acquisition parameters and/or reconstruction parameters. The acquisition parameters may relate to one or more conditions in obtaining scan data by, for example, scanning an object. The reconstruction parameters may relate to one or more conditions in reconstructing an image of the object. For example, the acquisition parameters may include a tube voltage, a tube current, recon parameters (e.g., a slice thickness), a scan time, a collimation/slice width, a beam filtration, a helical pitch, etc. The reconstruction parameters may include a reconstruction field of view (FOV), a reconstruction matrix, a convolution kernel/reconstruction filter, etc.

The controller 110 may control the imaging apparatus 102, the data acquisition module 104, the image reconstruction module 106, the console 108, and/or the storage device 112. For example, the controller 110 may control the imaging apparatus 102 to rotate to a desired position that may be prescribed by a user via the console 108. The controller 110 may control the parameters of radiation beams, including the intensity of radiation beams. As another example, the controller 110 may control the display of images on the console 108. In some embodiments, the controller 110 may control the data acquisition module 104 to acquire a signal generated from the imaging apparatus 102. Furthermore, the controller 110 may control the image reconstruction module 106 to generate an image based on data received from the data acquisition module 104.

The controller 110 may include a processor, a processing core, a memory, or the like, or a combination thereof. Specifically, the controller 110 may include a central processing unit (CPU), an application-specific integrated circuit (ASIC), an application-specific instruction-set processor (ASIP), a graphics processing unit (GPU), a physics processing unit (PPU), a digital signal processor (DSP), a field-programmable gate array (FPGA), a programmable logic device (PLD), a microcontroller unit, a microprocessor, an advanced RISC machines processor (ARM), or the like, or a combination thereof.

The storage device 112 may store data relating to the imaging system 100. The data may be a numerical value, an image, information of a subject, an instruction and/or a signal to operate the imaging apparatus 102, voice, a model relating to a patient, an algorithm relating to an image processing technique, or the like, or a combination thereof. Exemplary numerical values may include a threshold, a CT value, a value relating to an anti-scatter grid, or the like, or a combination thereof. Exemplary images may include a raw image or a processed image (e.g., an image after pretreatment). Exemplary models relating to a patient may include the background information of the patient, such as, ethnicity, citizenship, religion, gender, age, matrimony state, height, weight, medical history (e.g., history relating to different organs, or tissues), job, personal habits, or the like, or a combination thereof.

The storage device 112 may include a random access memory (RAM), a read-only memory (ROM), or the like, or a combination thereof. The random access memory (RAM) may include a dekatron, a dynamic random access memory (DRAM), a static random access memory (SRAM), a thyristor random access memory (T-RAM), a zero capacitor random access memory (Z-RAM), or the like, or a combination thereof. The read only memory (ROM) may include a bubble memory, a magnetic button line memory, a memory thin film, a magnetic plate line memory, a core memory, a magnetic drum memory, a CD-ROM drive, a hard disk, a flash memory, or the like, or a combination thereof. The storage device 112 may be a removable storage device such as a U flash disk that may read data from and/or write data to the image reconstruction module 106 in a certain manner. The storage device 112 may also include other similar means for providing computer programs or other instructions to operate the modules/units in the imaging system 100. The storage device 112 may be operationally connected with one or more virtual storage resources (e.g., a cloud storage, a virtual private network, other virtual storage resources, etc.) for transmitting or storing the data into the one or more virtual storage resources.

In some embodiments, the imaging system 100 may be connected to a network (not shown in the figure). The network may be a local area network (LAN), a wide area network (WAN), a public network, a private network, a proprietary network, a public switched telephone network (PSTN), the Internet, a virtual network, a metropolitan area network, a telephone network, or the like, or a combination thereof. The connection between different components in the imaging system 100 may be wired or wireless. The wired connection may include using a metal cable, an optical cable, a hybrid cable, an interface, or the like, or a combination thereof. The wireless connection may include using a wireless local area network (WLAN), a wireless wide area network (WWAN), a Bluetooth, a ZigBee, a near field communication (NFC), or the like, or a combination thereof.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the storage device 112 may be a database including cloud computing platforms, such as a public cloud, a private cloud, a community and hybrid clouds, etc. As another example, the data acquisition module 104 may be implemented on the imaging apparatus 102. As a further example, the controller 110 and the storage device 112 may be integrated into one module. However, those variations and modifications do not depart the scope of the present disclosure.

Figure 2:
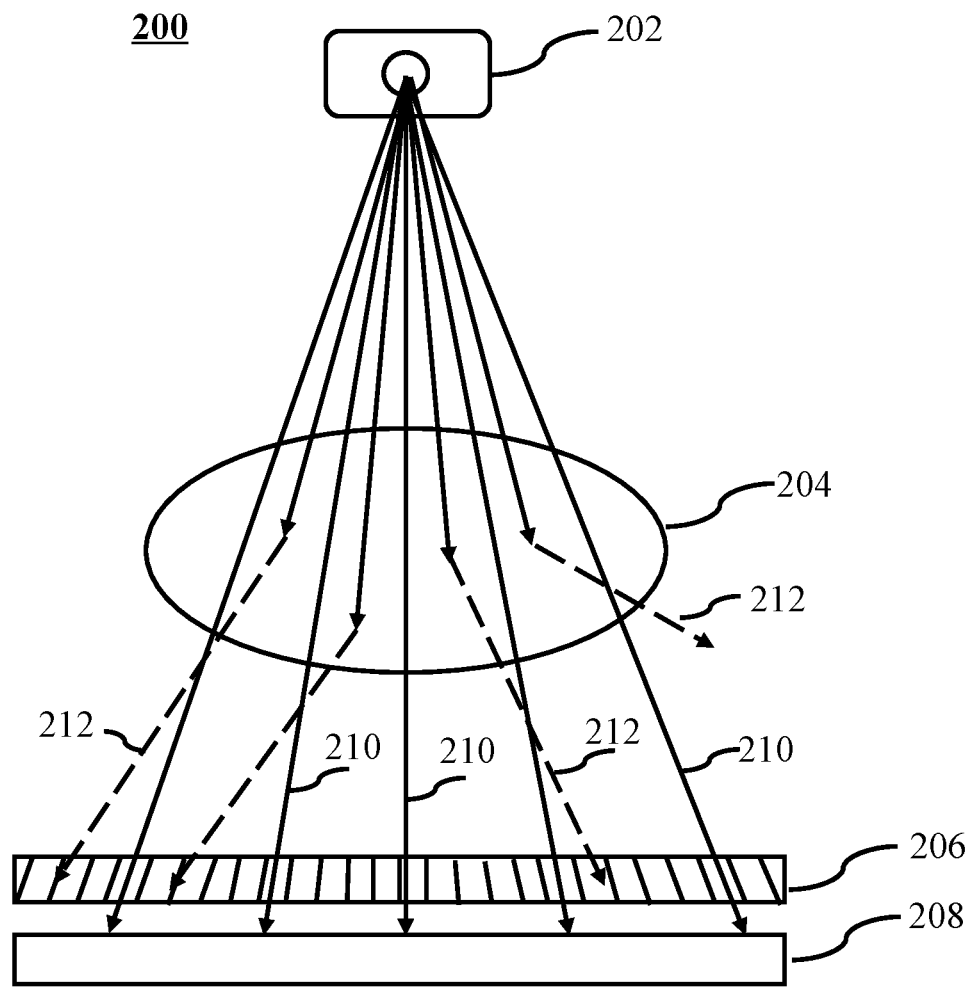
FIG. 2 is a schematic structure of an imaging apparatus according to some embodiments of the present disclosure.

FIG. 2 is a schematic structure of an imaging apparatus 200 according to some embodiments of the present disclosure. As shown, the imaging apparatus 200 may include a radiation source 202, an anti-scatter grid array 206, and a detector module 208.

The radiation source 202 may generate and emit radiation beams traveling toward an object 204. The radiation beams may include, for example, primary radiation beams 210 and secondary radiation beams 212 as shown in FIG. 2. A primary radiation beam 210 may refer to a radiation beam that travels along a substantially straight axis or direct trajectory between the radiation source 202 and the detector module 208. A secondary radiation beam 212 may refer to a radiation beam that is scattered or deflected while traversing the object 204 located in the pathway of the radition beam from the radiation source 202 to the detector module 208. The secondary radiation beams 212 may strike the detector module 208 at an angle relative to their original path(s) from the radiation source 202. In some embodiments, a secondary radiation beam 212 may also be referred to as a scattered radiation beam. While the primary radiation beams 210 are useful for generating an image of the object 204 under examination, the secondary radiation beams 212 may cause artifacts in the image.

The radiation source 202 may include a tube, such as a cold cathode ion tube, a high vacuum hot cathode tube, a rotating anode tube, etc. The tube may be powered by a high voltage generator. The tube may emit radiation beams toward the object 204 and/or the detector module 208. The detector module 208 may detect radiation beams passing through apertures in the imaging apparatus 200 defined by, for example, the anti-scatter grid array 206. Merely by way of example, the radiation beams may include X-rays, as described elsewhere in the disclosure. The object 204 may include a substance, a tissue, an organ, a specimen, a body, a human being, or the like, or a combination thereof as described elsewhere in the disclosure. The shape of the radiation beams emitted by the radiation source 202 may be a line, a pencil, a fan, a cone, a wedge, an irregular shape, or the like, or a combination thereof.

The anti-scatter grid array 206 may absorb scattered radiation. For example, the anti-scatter grid array 206 may absorb the secondary radiation beams 212 and/or alter directions of the secondary radiation beams 212, while allowing the primary radiation beams 210 to pass through the anti-scatter grid array 206. The types of radiation may include, for example, electromagnetic radiation, particle radiation, etc. The anti-scatter grid array 206 may include a material that can absorb one or more types of radiation (also referred to herein as a "highly absorbing material"). Exemplary highly absorbing materials may include tungsten, lead, uranium, gold, silver, copper, molybdenum, etc. The anti-scatter grid array 206 may also include a material that can allow one or more types of radiation to pass (also referred to herein as a "poorly absorbing material"). For example, the poorly-absorbing material may allow passage of essentially all radiation striking on the material. As used herein, "essentially all" may indicate that at least 50%, or at least 60%, or at least 70%, or at least 80%, or at least 90%, or at least 95% of the radiation striking on the poorly absorbing material may pass through. As another example, the poorly absorbing materials may be substantially non-absorbent of certain radiation. For instance, all or a certain amount of the radiation striking on a poorly absorbing material may pass through the material. Merely by way of example, at least 50%, or at least 60%, or at least 70%, or at least 80%, or at least 90%, or at least 95% of the radiation striking on the poorly absorbing material may pass through the material. Examples of the poorly absorbing materials may include resin, a fibrous material, rubber, an inorganic non-metallic material (e.g., ceramics), etc. The resin may include thermoplastic resin or thermosetting resin. The thermosetting resin may include phenolic resin, urea-formaldehyde resin, melamine-formaldehyde resin, epoxy resin, unsaturated resin, polyurethane, polyimide, etc. The thermoplastic resin may include polymethyl methacrylate (PMMA), acrylonitrile butadiene styrene (ABS), polyamide, polylactic acid (PLA), polybenzimidazole (PBI), polycarbonate (PC), polyethersulfone (PES), polyetheretherketone (PEEK), polyethylene (PE), polyphenylene oxide (PPO), polyphenylene sulfide (PPS), polypropylene (PP), polystyrene (PS), polyvinyl chloride (PVC), etc. The fibrous material may include an inorganic fibrous material, an organic fibrous material, or the like, or a combination thereof. Exemplary inorganic fibrous material may include glass fibers, carbon fibers, boron fibers, whisker, asbestos fibers, silicon carbide fibers, etc. Organic fibers may include synthetic fibers including, for example aramid fibers, polyester fibers, nylon fibers, vinylon fibers, polypropylene fibers, polyimide fibers, etc., and natural fiber (e.g., cotton, sisal, paper) etc. The rubber may include butyl rubber, chlorinated rubber, nitrile rubber, etc.

A highly absorbing material and a poorly absorbing material may absorb different amounts of radiation. For example, the highly absorbing material may absorb a greater amount of radiation than the poorly absorbing material. The highly absorbing material(s) and/or the poorly absorbing material(s) may be positioned in the anti-scatter grid array 206 to absorb scattered radiation. For example, plates made of the highly absorbing materials may be positioned parallel to and/or substantially parallel to paths of radiation beams from the radiation source 202 to the detector module 208. The highly absorbing materials may absorb scattered radiation beams (e.g. secondary radiation beams 212). The poorly absorbing material may allow primary radiation beams (e.g., primary radiation beams 210) to pass through the anti-scatter grid array 206.

In some embodiments, the anti-scatter grid array 206 may be placed between the radiation source 202 and the detector module 208. The anti-scatter grid array 206 may be coupled to the detector module 208. For example, the anti-scatter array grid 206 may be coupled to the detector module 208 by bonding, gluing, taping, welding, etc. One or more fasteners may be used to connect the anti-scatter grid array 206 to the detector module 208. Exemplary fasteners may include a rivet, a bolt, a pin joint, a key joint, or the like, or a combination thereof.

The shape of the anti-scatter grid array 206 may be flat, arc-shaped, circular, linear, or the like, or a combination thereof. Examples of the anti-scatter grid array 206 may include a focused grid (e.g., an arc-focused grid), a linear grid, a crossed grid, a parallel grid, or the like, or a combination thereof. In some embodiments, the anti-scatter grid array 206 may include a specific configuration defined by one or more parameters, such as a focal length, a grid ratio, a grid density, etc. For example, a highly absorbing material may be configured as a plate. The focal length may refer to a perpendicular distance from the focal point to the upper surface of the anti-scatter grid array 206. The focal point of the anti-scatter grid array 206 may be a point at which a plurality of plates of the anti-scatter grid array 206 meet. The plates of the highly absorbing material(s) may be placed at various positions based on the focal length of anti-scatter grid 206. In some embodiments, an offset angle of a plate of the anti-scatter grid arrary 206 may be determined. The offset angle of a plate may be set such that the primary radiation beams 210 is not blocked by the plate, while the secondary radiation beams 212 may be blocked by or strike the plate. The offset angle may be defined as an angle between a path of a primary radiation beam 210 emitted from the radiation source 202 and the normal line that is perpendicular to the upper surface of the anti-scatter grid 206. The grid ratio may be a ratio of the height of the plate to an interspace between adjacent plates.

In some embodiments, the anti-scatter grid array 206 may include one or more anti-scatter grid modules. Each anti-scatter grid module may be a focused grid, a rectilinear grid, a crossed grid, an arc grid, a parallel grid, or the like, or a combination thereof. Each anti-scatter grid module may be in a specific configuration defined by one or more parameters, including a focal length, a grid ratio, a grid density, etc. In some embodiments, the anti-scatter grid modules of the anti-scatter grid array 206 may have the same configuration defined by the same parameters. In some embodiments, at least some of the anti-scatter grid modules may have different configurations defined by different parameters. In some embodiments, the anti-scatter grid modules may attach to each other by bonding, gluing, taping, welding, etc. In some embodiments, one or more fasteners may be used to connect the anti-scatter grid array 206 to the detector module 208. Exemplary fasteners may include a rivet, a bolt, a pin joint, a key joint, or the like, or a combination thereof.

The detector module 208 may detect radiation beams traversing the object 204. The detector module 208 may include one or more detector sub-modules. In some embodiments, a plurality of detector sub-modules of the detector module 208 may be positioned to form an arcuate structure. A detector sub-module may include a plurality of pixels. A pixel may refer to the smallest unit in the detector module 208 that may detect radiation beams. One or more detector sub-modules may be detachably assembled to form the detector module 208. The width of the detector module 208 may be the sum of the width of each detector sub-module of the detector module 208. The number of the detector sub-modules may be fixed or adjustable according to different conditions including, for example, a desired resolution of an image, a desired size of an image, the size of an object, the sensitivity of the detector sub-modules, the mechanical stability of the detector sub-modules, or the like, or a combination thereof.

The detector module 208 may have any suitable shape. For example, the shape of the detector module 208 may be flat, arc-shaped, circular, or the like, or a combination thereof. The fan angle of an arc-shaped detector module may have any suitable value. The fan angle may be in the range from 0° to 360°, from 30° to 270°, from 45° to 300°, etc. The fan angle of the arc-shaped detector may be above 30°. The fan angle of the arc-shaped detector may be above 45°. The fan angle of the arc-shaped detector may be one of 45°, 60°, 75°, 90°, or 105°.

The detector module 208 may include a detection layer. The detection layer may include, e.g., a scintillator layer and a photodiode array. The scintillator layer may generate a visible light when detecting a radiation beam. The photodiode array may convert the visible light into an electrical signal. The scintillator layer may include a plurality of scintillators disposed in a matrix form in a plane. For example, a detector sub-module may include a matrix of 32×64 scintillators. The photodiode array may include a plurality of photodiodes disposed in a matrix form in a plane parallel to and/or substantially parallel to the plane of the scintillator layer. As used herein, "substantially parallel" may indicate that the angle between the plane formed by the photodiode array and the plane of the scintillator layer is close to zero, e.g., less than 60 degrees, or less than 50 degrees, or less than 40 degrees, or less than 30 degrees, or less than 20 degrees, or less than 10 degrees, or less than 5 degrees. For example, a detector sub-module may include a matrix of 32×64 photodiodes. In some embodiments, the detector layer may convert the radiation beams impinging thereon into an electrical signal directly by a suitable material, such as amorphous selenium.

The detector module 208 may include at least one data acquisition circuitry that may process the electrical signal received from the array of photodiodes. For example, the at least one data acquisition circuitry may convert the electrical signal to a digital signal for further processing. In some embodiments, the at least one data acquisition circuitry may be electrically connected with a portion of the detector module 208, such as a portion of or all the plurality of photodiodes of the detector module 208. For example, the plurality of photodiodes of the detector module 208 may be electrically connected with the at least one data acquisition circuitry through one or more signal transmission boards. The number of the plurality of signal transmission boards connected to a data acquisition circuitry may be fixed or adjustable according to different conditions including, for example, the heat dissipation need, the ambient temperature, the sensitivity of the detector sub-modules, the stability of the detector sub-modules, or the like, or a combination thereof.

Figure 13:
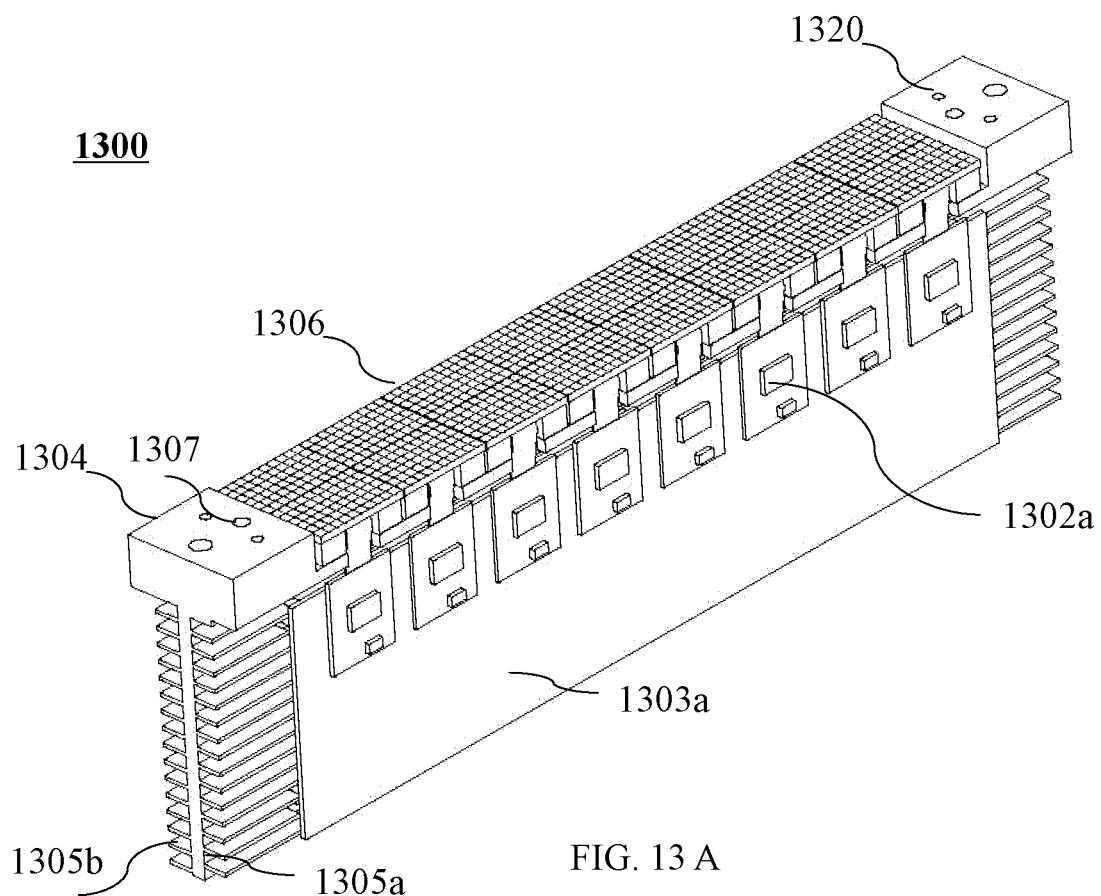
FIGS. 13A and 13B illustrate a perspective view and a side view of an exemplary detector sub-module according to some embodiments of the present disclosure.
Figure 13:
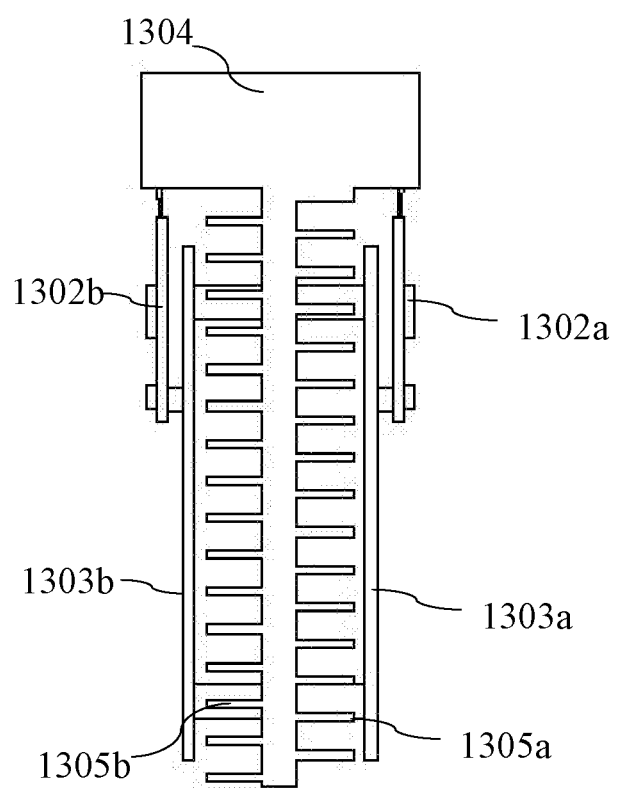

The detector module 208 may include a frame that supports the detection layer and the data acquisition circuitry. The frame may have any suitable shape and/or dimension. For example, the cross-section of the frame may have the shape of a rectangle, a trapezoid, a polygon, or any other regular or irregular shape. In some embodiments, the frame may have a shape like a capital T as illustrated in FIGS. 13A and 13B. The frame may have a base part that is physically attached to the detection layer, and a columnar part that is perpendicular to and/or substantially perpendicular to the base part. As used herein, "substantially perpendicular" may indicate that the angle between the column part and the base part is close to 90 degrees or the deviation (from 90 degrees) is less than 50 degrees, or less than 40 degrees, or less than 30 degrees, or less than 20 degrees, or less than 10 degrees, or less than 5 degrees. In some embodiments, different frames of different detector sub-modules may be attached to each other to form a detector module. For instance, the frames of any two neighboring detector sub-modules are attached to each other by way of, for example, bonding, gluing, taping, welding, fasteners, or the like, or a combination thereof. In some embodiments, the frames of different detector sub-modules may be mounted on a supporting structure, such as a baseboard. The supporting structure may hold different detector sub-modules together to form a detector module.

The detector module 208 may include a plurality of heat transfer fins to facilitate the dissipation of the heat produced by the detection layer, and/or the at least one electrical circuitry attached to the detection layer.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For instance, the anti-scatter grid array 206 may be an integrated part of the detector module 208. However, those variations and modifications do not depart the scope of the present disclosure.

Figure 3:
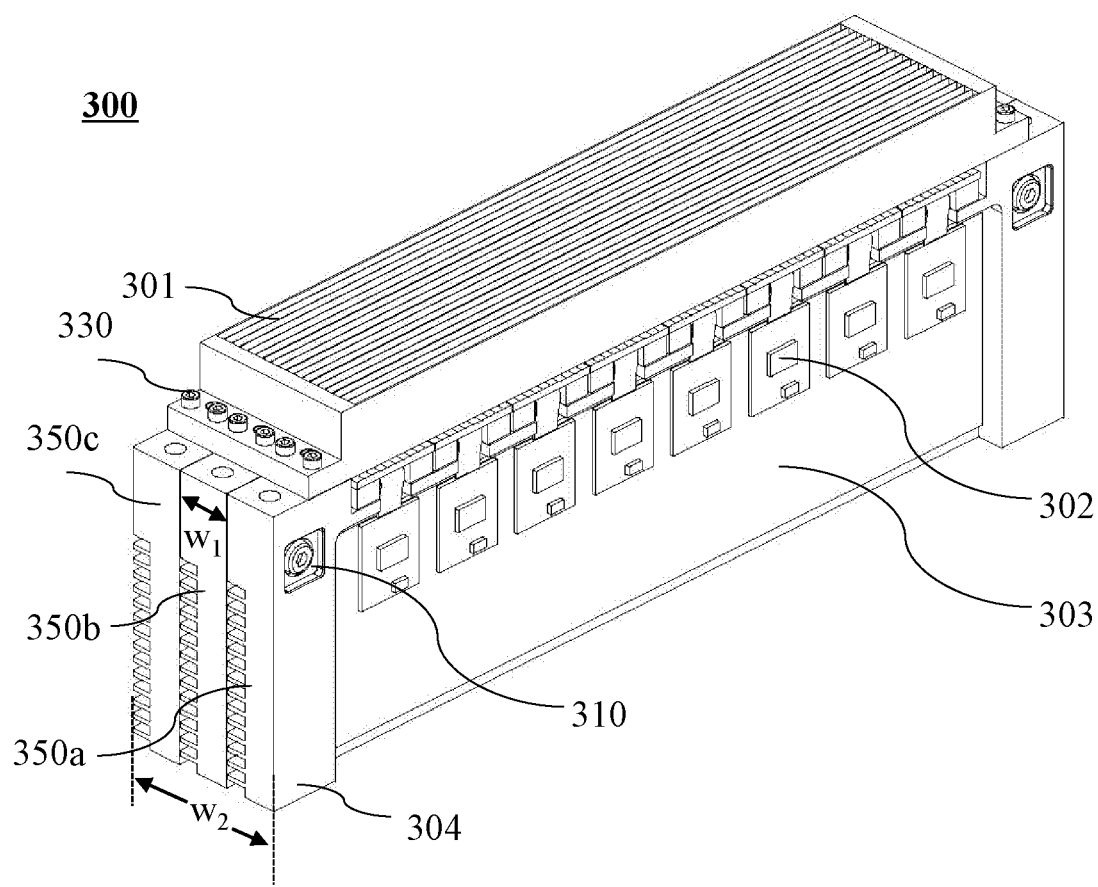
FIG. 3 illustrates a perspective view of an exemplary detector module according to some embodiments of the present disclosure.

FIG. 3 illustrates a perspective view of an exemplary detector module according to some embodiments of the present disclosure. As shown, the detector module 300 may include an anti-scatter grid 301, a bolt 310, a threaded fastener 330, a first detector sub-module 350a, a second detector sub-module 350b, and a third detector sub-module 350c. The anti-scatter grid 301 may be located at the top of the detector module 300. The first detector sub-module 350a may be located at one end of the detector module 300, e.g., the front end of the detector module 300 as shown in FIG. 3. The third detector sub-module 350c may be located at another end of the detector module 300, e.g., the rear end of the detector module 300 as shown in FIG. 3. The second detector sub-module 350b may be located between the first detector sub-module 350a and the third detector sub-module 350c. The bolt 310 may be inserted through the first detector sub-module 350a, the second detector sub-module 350b, and the third detector sub-module 350c.

In some embodiments, the anti-scatter grid 301 may include a highly absorbing material as described in connection with FIG. 2. In some embodiments, the anti-scatter grid 301 may be made of a polymer-based composite material including high-density particles of one or more highly absorbing materials that can absorb radiation. In some embodiments, the anti-scatter grid 301 may be made of an alloy including at least one highly absorbing material. In some embodiments, the width of the anti-scatter grid 301 may be the same as the width $w_2$ of the detector module, e.g., one side of the anti-scatter grid 301 aligns with the corresponding side of the first detector sub-module 350a, and the opposing side of the anti-scatter grid 301 aligns with the corresponding side of the third detector sub-module 350c as shown in FIG. 3. The width $w_2$ of the detector module may be the sum of the widths of each detector sub-module that forms the detector module, e.g., the first detector sub-module 350a, the second detector sub-module 350b, and the third detector sub-module 350c.

In some embodiments, a detector sub-module may include a detection layer, a data acquisition circuitry, a plurality of signal transmission boards, a frame, and a plurality of heat transfer fins as described in connection with FIG. 2. The width of a detector sub-module, e.g., the width $w_1$ of the second detector sub-module 350b, may be equal to or smaller than the width of the detection layer. In some embodiments, the widths of different detector sub-modules may be the same or different. For example, the width of the detector sub-module located at an end of the detector module (e.g., the first detector sub-module 350a, the third detector sub-module 350b) may be the same as or different from the width of the detector sub-module located in the middle portion of the detector module (e.g., the second detector sub-module 350b).

The threaded fastener 330 may be used to mount the anti-scatter grid 301 on the top of the detector sub-modules, as described in connection with the threaded fastener 430 in FIG. 4.

A sub-module may include components that are used to, for example, connect to another detector sub-module, and/or process a signal generated in response to impinged radiation beams. For illustration purposes, the structure of the first detector sub-module 350a is described as an example. The first detector sub-module 350a may include a detection layer (not shown in FIG. 3), a plurality of signal transmission boards 302 (eight signal transmission boards 302 are shown in FIG. 3 for illustration purposes), and a data acquisition circuitry 303. Radiation beams that pass through the anti-scatter grid 301 may impinge on the dection layer where an electrical signal may be generated in response. The plurality of signal transmission boards 302, each connecting to a portion of the detection layer, may transmit the electrical signal from corresponding portions of the detection layer to the data acquisition circuitry 303. The data acquisition circuitry 303 may process the electrical signals, such as convert the electrical signals to digital signals for further processing. Furthermore, the first detector sub-module 350a may include a frame 304 that supports the detection layer, the anti-scatter grid 301, the data acquisition circuitry 303, etc. The frame 304 may include a positioning element configured to facilitate the assembling of the detector module 300. For instance, a first frame of two neighboring (or adjacent) frames 304 may include a boss (or protrusion), while a second frame of the two neighboring frames 304 may include a recessed pocket that is complementary to the boss of the first frame such that the two neighboring frames 304 may be attached to each other by insert the boss into the recessed pocket. As used herein, a boss may be considered complementary to a recessed pocket if the boss and the recessed pocket may form a mating connection (the boss may be also referred to as male connector, and the recessed pocket may be also referred to as female connector). Merely by way of example, the recessed pocket of the second detector sub-module 350b may receive the boss of the first detector sub-module 350a. Then, the first detector sub-module 305a and the second detector sub-module 305b may be assembled by inserting the bolt 310 through the hole defined in the boss of the first detector sub-module 350a and the corresponding hole defined in the recessed pocket of the second detector sub-module 350b. The bolt 310 may be further fastened by a nut.

It shall be noted that any two adjacent detector sub-modules may be assembled via a boss of one detector sub-module and a recessed pocket of the other detector sub-module. In some embodiments, the detector sub-modules at an end of the detector module may include at least one of a boss and a recessed pocket. For example, the first detector sub-module 350a may at least include a boss that is complementary to a recessed pocket of the second detector sub-module 350b. The third detector sub-module 350c may at least include a recessed pocket that is complementary to a boss of the second detector sub-module 350b. The detector sub-module in the middle of the detector module may at least include a pair of the boss and the recessed pocket, each located on a side of the detector sub-module that faces an adjacent detector sub-module, respectively. For instance, the detector sub-module 350b may include a recessed pocket on the one side facing the first detector sub-module 350a, and a boss on the opposite side facing the third detector sub-module 350c.

In some embodiments, the boss and/or recessed pocket may be replaced by other structures that may facilitate assembly (e.g., facilitate alignment and/or attachment) of the detector sub-modules. For example, the detector sub-modules may be assembled by fixing the detector sub-modules on one or more baseboards.

In some embodiments, different alignment techniques may be used in the assembling of a detector module. For example, a first alignment technique, e.g., using aligning structures, may be used to assemble a first pair of adjacent detector sub-modules, and a second alignment technique, e.g., bonding via a glue layer, may be used to assemble a second pair of adjacent detector sub-modules. In some embodiments, the glue layer may be distributed between the two adjacent detector sub-modules uniformly to keep the adjacent detector sub-modules contact as close as possible. In some embodiments, the glue layer may be applied non-uniformly or only to a portion of the surfaces where the adjacent detector sub-modules meet.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. In some embodiments, the anti-scatter grid 301 may be assembled by a plurality of anti-scatter sub-grids. Each of the anti-scatter sub-grids may correspond to a detector sub-module. However, those variations and modifications do not depart the scope of the present disclosure.

Figure 4:
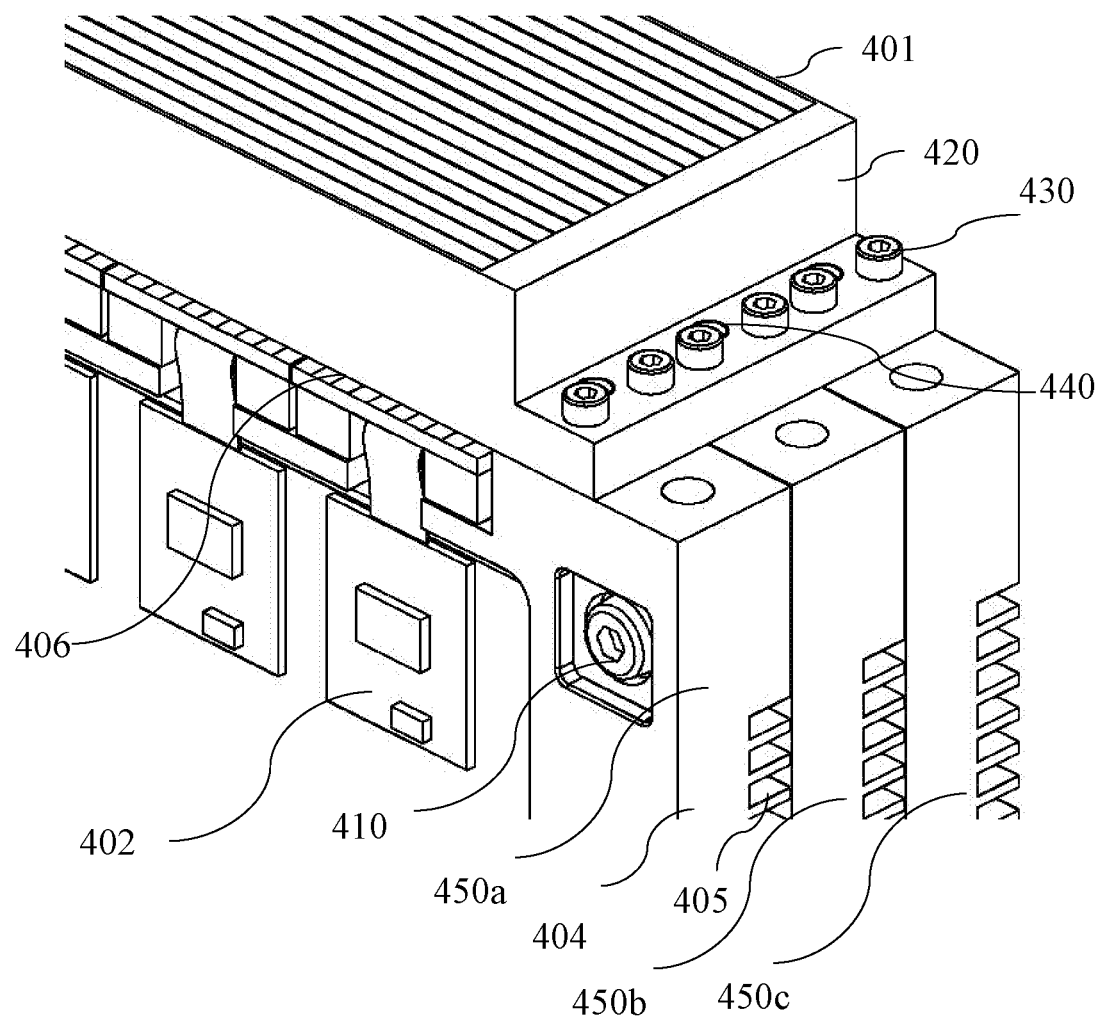
FIG. 4 illustrates a perspective view of an exemplary anti-scatter grid module of a detector module according to some embodiments of the present disclosure.

FIG. 4 illustrates a perspective view of an exemplary detector module according to some embodiments of the present disclosure. As shown, the detector module 400 may include an anti-scatter grid 401, a detection layer 406, a bolt 410, an anti-scatter grid supporting block 420, a threaded fastener 430, an alignment pin 440, a first detector sub-module 450a, a second detector sub-module 450b, and a third detector sub-module 450c. The first detector sub-module 450a may include a plurality of signal transmission boards 402, a frame 404, and a plurality of heat transfer fins 405.

The anti-scatter grid 401 may include a plurality of anti-scatter plates. The anti-scatter plates may include a highly absorbing material that absorbs one or more types of radiation. A pair of adjacent anti-scatter plates may be spaced by an interspace. The interspace between two adjacent plates may be filled with air or a poorly absorbing material. In some embodiments, the anti-scatter grid plates of the anti-scatter grid 401 may be equally spaced.

The anti-scatter grid supporting block 420 may provide a sidewall for the anti-scatter grid 401. The anti-scatter grid supporting block 420 may include a poorly absorbing material that can allow one or more types of radiation to pass (e.g., X-rays, alpha rays, etc.).

The bolt 410 may be used to assemble the detector module 400 as described elsewhere in the disclosure. See, for example, the bolt 310 described in connection with FIG. 3.

Radiation beams that pass through the anti-scatter grid 401 may impinge on the detection layer 406. Details regarding the detection layer may be found elsewhere in the disclosure. See, for example, the detection layer 606 described in connection with FIG. 6.

The threaded fastener 430 may be used to fix the anti-scatter grid 401 on the frame(s) of the first detector sub-module 450a, the second detector sub-module 450b, and/or the third detector sub-module 450c. The threaded fastener 430 may be inserted through the anti-scatter grid 401 and at least partially into the frame(s) of the first detector sub-module 450a, the second detector sub-module 450b, and/or the third detector sub-module 450c. In some embodiments, the threaded fastener 430 may be part of a rivet structure, a key joint, a pin joint, and/or any other fastening mechanism.

The alignment pins 440 may be used to align the anti-scatter grid 401 with the first detector sub-module 450a, the second detector sub-module 450b, and/or the third detector sub-module 450c. In some embodiments, the alignment pin 440 may be inserted into a pin hole on the frame of a detector sub-module, such as pin hole 507 as illustrated in FIG. 5.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the anti-scatter grid 401 may be assembled based on a plurality of anti-scatter sub-grids, and the assembled anti-scatter grid 401 may be further connected to the detector sub-modules. However, those variations and modifications do not depart the scope of the present disclosure.

Figure 5:
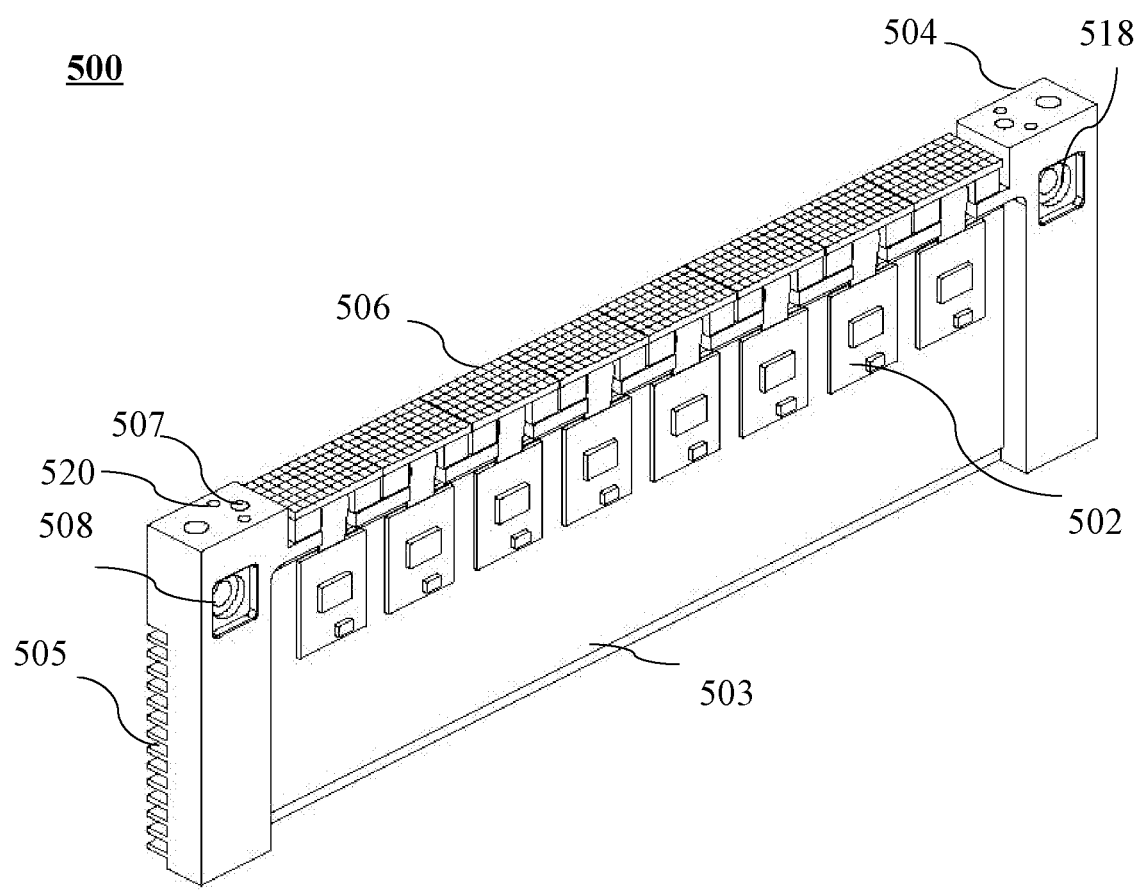
FIG. 5 illustrates a perspective view of a detector sub-module according to some embodiments of the present disclosure.

FIG. 5 illustrates a perspective view of a detector sub-module according to some embodiments of the present disclosure. As shown, the detector sub-module 500 may include a plurality of signal transmission boards 502, a data acquisition circuitry 503, a frame 504, a plurality of heat transfer fins 505, a detection layer 506, a pin hole 507, a plurality of threaded holes 520, a first recessed pocket 508, and a second recessed pocket 518. In some embodiments, the detector sub-module may be the first detector sub-module, the second detector sub-module, or the third detector sub-module as described in connection with FIG. 3.

The plurality of signal transmission boards 502 may be configured to transmit electrical signals received from the detection layer 506 to the data acquisition circuitry 503. As shown in FIG. 5, each of the plurality of signal transmission boards 502 may be electrically connected with a different portion of the detection layer 506. The electrical signals from each of the plurality of signal transmission boards 502 may be processed by the data acquisition circuitry 503. In some embodiments, the plurality of signal transmission boards 502 may be located on the same side of the data acquisition circuitry 503. An electrical connection between a signal transmission board 502 and the data acquisition circuitry 503 may be formed. See, e.g., relevant description of FIGS. 7A and 7B. In some embodiments, the plurality of signal transmission boards 502 may be located on different sides of the data acquisition circuitry 503. See, for example, the signal transmission boards 1202a and 1202b in FIG. 12B. In some embodiments, the plurality of signal transmission boards 502 may include a circuit printed on a flexible plastic substrate, such as polyimide, transparent conductive polyester film, etc.

The data acquisition circuitry 503 may be configured to process the electrical signal from the plurality of signal transmission boards 502. In some embodiments, the data acquisition circuitry 503 may be fixed on the frame 504 by bonding, gluing, taping, welding, etc. In some embodiments, the data acquisition circuitry 503 and the frame 504 may be connected using any suitable fastener, such as rivets, bolts, bolts, pins joints, key joints, or the like, or a combination thereof.

The frame 504 may be configured to support the components of the detector sub-module 500, such as the data acquisition circuitry 503, the detection layer 506, etc. The frame 504 may have any suitable shape and/or dimension. For example, the cross-section of the frame may have a shape of a rectangle, a trapezoid, a polygon, or any other regular or irregular shape. In some embodiments, the frame may have a shape like a capital T as described in connection with FIGS. 13A and 13B. The frame may have a base part that is attached to the detection layer 506, and a columnar part that is perpendicular to and/or substantially perpendicular to the base part. The columnar part may be disposed at one side of the base part as described in connection with FIG. 5, or may be disposed in the middle of the base part as described in FIGS. 13A and 13B.

The plurality of heat transfer fins 505, forming a heat dissipation structure, may be thermally connected or coupled with one or more other parts of the detector sub-module 500A. As used herein, that a first structure is thermally connected or coupled with a second structure may indicate that heat may transfer between the first structure and the second structure. In some embodiments, the plurality of heat transfer fins 505 may facilitate the dissipation of the heat produced by the data acquisition circuitry 503 and/or the detection layer 506. The plurality of heat transfer fins 505 may be disposed on one or more sides of the frame 504. For example, the plurality of heat transfer fins 505 may be disposed on a same side of the columnar part of the frame 504, as shown in FIG. 5. As another example, the plurality of heat transfer fins 505 may be disposed on opposite sides of the frame 504. See, for example, heat transfer fins 1305a and 1305b in FIGS. 13A and 13B. The plurality of heat transfer fins 505 may be evenly or unevenly arranged along the columnar part of the frame 504. In some embodiments, an interspace between two heat transfer fins may be filled with air. In some embodiments, an interspace between two heat transfer fins may be filled with an effective heat dissipation material. In some embodiments, an interspace between two heat transfer fins may be filled partially with air and partially with an effective heat dissipation material. Exemplary effective heat dissipation materials may include an alloy, a carbon fiber, a graphite, a thermal conductive adhesive, a thermally conductive grease, etc. In some embodiments, the plurality of heat transfer fins 505 may form an integral part of the frame 504. For example, the transfer fins 505 and the frame 504 may be manufactured together as a one-piece or integral component. As another example, the transfer fins 505 may be welded to the frames 504. In some embodiments, the plurality of heat transfer fins 505 may be mounted on the frame via a mechanically connection. For example, the plurality of heat transfer fins 505 may be fixed on the frame 504 using a bolt. As another example, the plurality of heat transfer fins 505 may be inserted into one or more slots in the frame 504.

A heat transfer fin 505 may have any suitable shape and/or dimension. For example, the cross-section of a heat transfer fin 505 may have the shape of a rectangle, a trapezoid, a polygon, or any other regular or irregular shape. In some embodiments, the plurality of heat transfer fins 505 may be arranged in a manner that each fin may form an angle with respect to, for example, the horizontal line. In some embodiments, the heat transfer fins may be parallel to and/or substantially parallel to each other. As used herein, "substantially parallel" may indicate that the angle between the heat transfer fins is close to zero, e.g., less than 60 degrees, or less than 50 degrees, or less than 40 degrees, or less than 30 degrees, or less than 20 degrees, or less than 10 degrees, or less than 5 degrees.

The detection layer 506 may include a scintillator layer and a photodetector layer. The scintillator layer may convert the radiation beams into an optical signal. The photodetector layer may include a plurality of photodiodes that convert the optical signal into an electrical signal.

The plurality of pin holes 507 may be configured to align the frame 504 with an anti-scatter grid as described in FIG. 4. The plurality of pin holes 507 may be configured to receive one or more alignment pins that pass through the sidewalls of the anti-scatter grid as described in connection with FIG. 4. A pin hole 507 may have any suitable shape and/or dimension. For example, a pin hole 507 may have the shape of a circle, an ellipse, a hexagon or any other regular or irregular shape.

The first recessed pocket 508 and/or the second recessed pocket 518 may be configured to align the detector sub-module with another detector sub-module. The other detector sub-module may have a complementary positioning element, such as a boss. The shape of a boss may be complementary to the shape of the first recessed pocket 508 and/or the second recessed pocket 518. For example, the first recessed pocket 508 and/or the second recessed pocket 518 may be configured to facilitate the alignment and/or attachment between the second detector sub-module 350b and the third detector sub-module 350c as described in connection with FIG. 3.

The first recessed pocket 508 and/or the second recessed pocket 518 may have any suitable shape and/or dimension. For example, the cross-section of the first recessed pocket 508 and/or the second recessed pocket 518 may have the shape of a rectangle, a trapezoid, a polygon, a circle, an ellipse, or any other irregular shape. There may be one or more holes in the first recessed pocket 508 and/or the second recessed pocket 518. A fastener (e.g., a bolt) may be inserted into such a hole to facilitate the assembly of a plurality of detector sub-modules.

In some embodiments, there may be any suitable number of recessed pockets in a frame. Merely by way of example, there may be two recessed pockets located in a frame. The first recessed pocket 508 may be located on one side of the frame, and the second recessed pocket 518 may be located on the opposite side of the frame as illustrated in FIG. 5.

The plurality of threaded holes 520 may be configured to assemble the frame 504 and an anti-scatter grid as described in FIG. 4. The plurality of threaded holes 520 may be configured to receive one or more threaded fasteners as described in connection with FIG. 4. A threaded hole 520 may have any suitable shape and/or dimension. For example, the cross-section of a threaded hole 520 may have the shape of a circle, an ellipse, a hexagon or any other regular or irregular shape.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the detection layer 506 may be disposed at the top of the frame 504 by way of bonding, gluing, taping, welding, a fastener, or the like, or a combination thereof. However, those variations and modifications do not depart the scope of the present disclosure.

Figure 6:
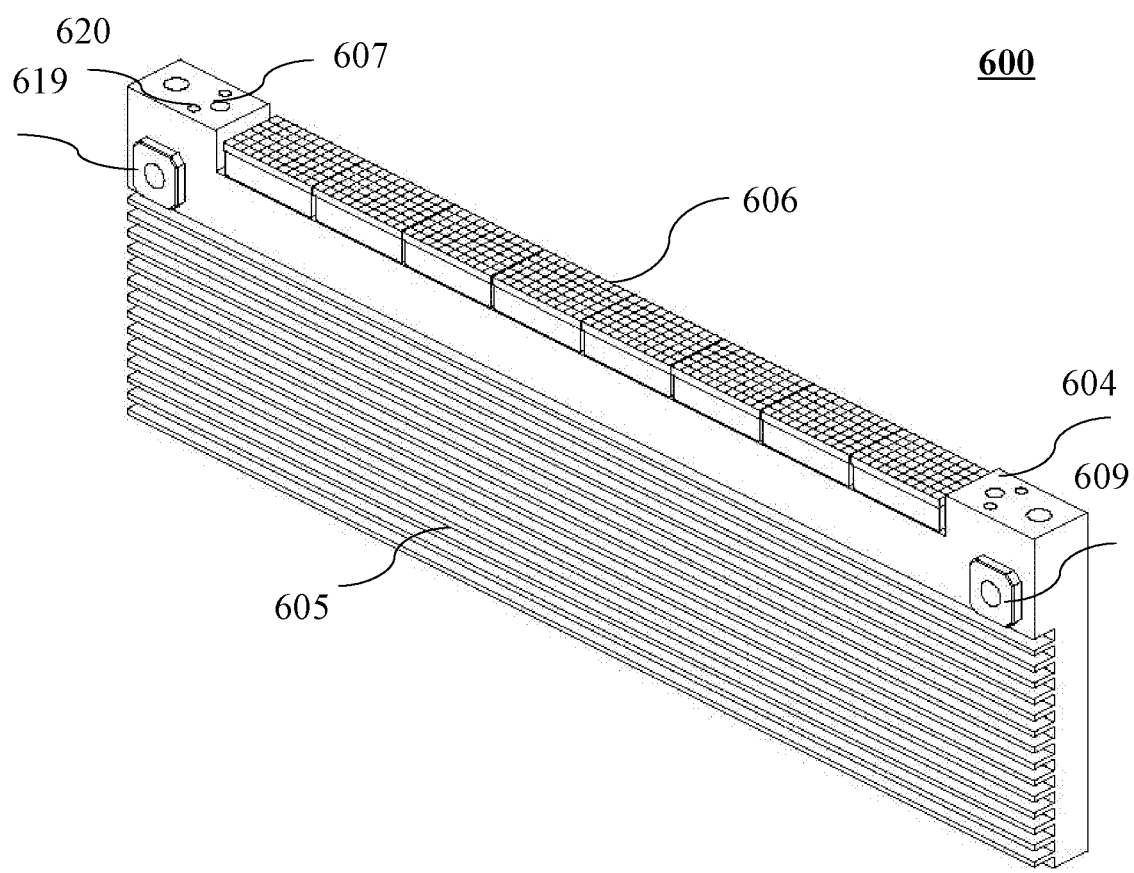
FIG. 6 illustrates a perspective view of another detector sub-module according to some embodiments of the present disclosure.

FIG. 6 illustrates a perspective view of a detector sub-module 600 according to some embodiments of the present disclosure. As shown, the detector sub-module 600 may include a frame 604, a plurality of heat transfer fins 605, a detection layer 606, a pin hole 607, a first boss 609, a second boss 619, and a plurality of threaded holes 620. The frame 604, the plurality of heat transfer fins 605, the detection layer 606, the pin hole 607, and the plurality of threaded holes 620 may be similar to the frame 504, the plurality of heat transfer fins 505, the detection layer 506, the pin hole 507, and the plurality of threaded holes 520, and the description is not repeated here.

In some embodiments, the detector sub-module 600 may correspond to the first detector sub-module, the second detector sub-module, or the third detector sub-module as described in FIG. 3. The first boss 609 and/or the second boss 619 may have any suitable shape and/or dimension. For example, the cross-section of the first boss 609 and/or the second boss 619 may have the shape of a rectangle, a trapezoid, a polygon, a circle, an ellipse, or any other irregular shape. The shape of the first boss 609 may be complementary to the shape of a recessed pocket, such as the first recessed pocket 508 of another detector sub-module. There may be one or more holes in the first boss 609 and/or the second boss 619. A fastener (e.g., a bolt) may be inserted into such a hole to facilitate the assembly of a plurality of detector sub-modules.

In some embodiments, there may be any suitable number of bosses on a frame. Merely by way of example, there may be two bosses located on a frame. The first boss 609 may be located on one side of the frame and the second boss 619 may be located on the opposite side of the frame as illustrated in FIG. 6. The number of bosses on a detector sub-module may be same with the number of recessed pockets on another detector sub-module that is attached to the detector sub-module.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the detection layer 606 may be connected to an anti-scatter grid by a glue layer, a rivet, or the like, or a combination thereof. However, those variations and modifications do not depart the scope of the present disclosure.

Figure 7A:
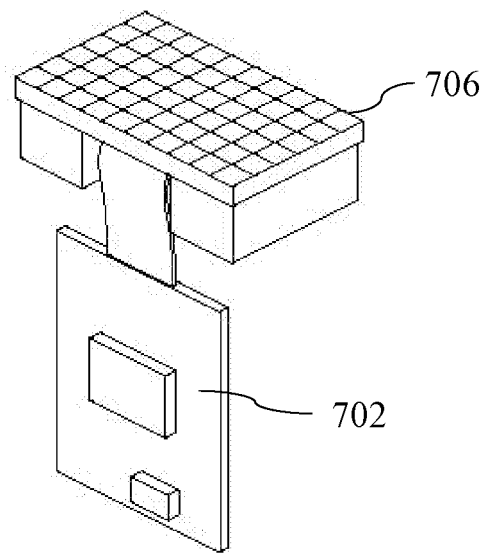
FIGS. 7A and 7B are perspective views of a portion of a detector sub-module according to some embodiments of the present disclosure.
Figure 7B:
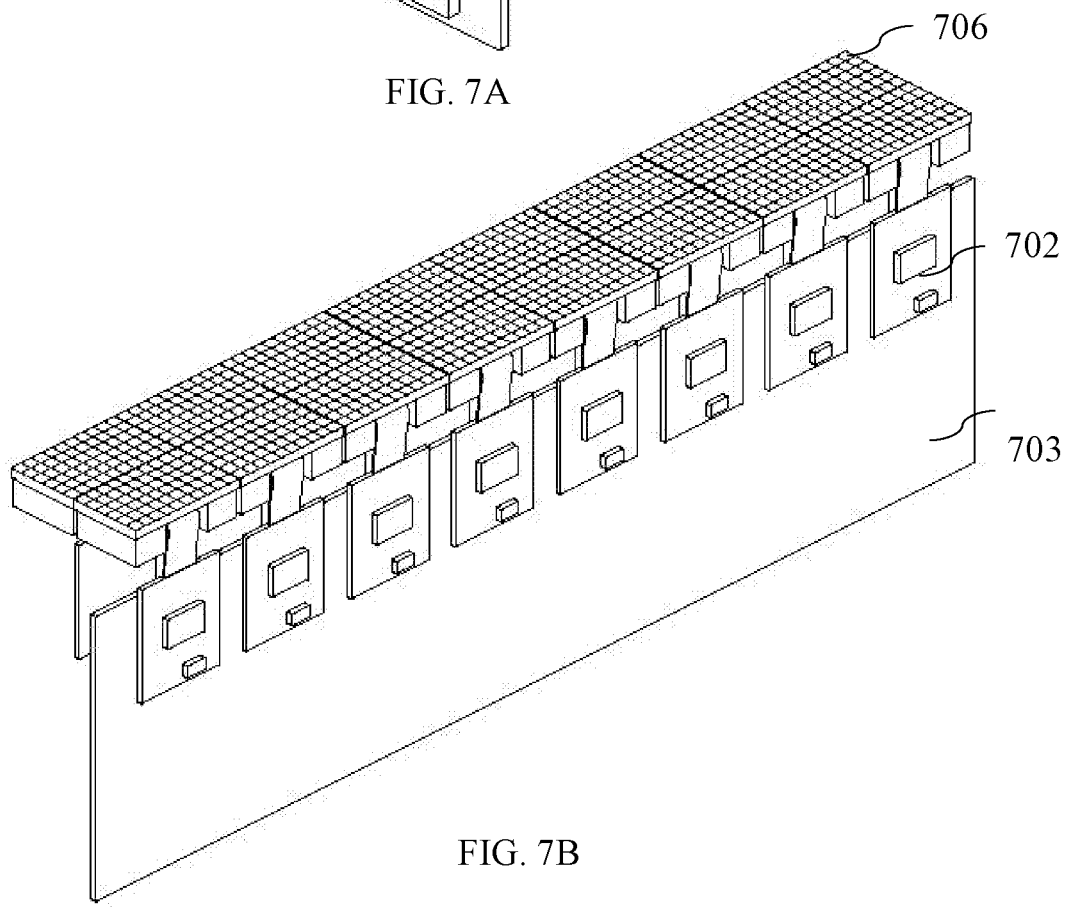

FIGS. 7A and 7B are perspective views of a portion of a detector sub-module according to some embodiments of the present disclosure. As shown, a detection layer 706 may be electrically connected to a signal transmission board 702. The signal transmission board 702 may be further electrically connected to a data acquisition circuitry 703.

The detection layer 706 may include a plurality of pixels. A pixel may include a scintillator and a photodetector. The plurality of pixels may be disposed in a matrix form. Merely by way of example, the detection layer 706 may include a matrix of 64×512 pixels. The 64×512 pixels may be divided into 16 groups of pixels, each of which may include 32×64 pixels. The 16 groups of pixels may be arranged in two rows so that each row may have 8 groups of pixels. In some embodiments, a group of pixels may be connected to a signal transmission board, e.g., the signal transmission board 702. In some embodiments, two or more groups of the pixels may be connected to a same signal transmission board.

As shown in FIG. 7B, the plurality of signal transmission boards, including the signal transmission board 702, may be disposed on a same side of the data acquisition circuitry 703. It shall be noted that the plurality of signal transmission boards may be disposed on different sides of the data acquisition circuitry 703, including the front side and the rear side. The number of signal transmission boards 702 located on each side may be the same or different.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the detection layer 706 may be connected to an anti-scatter grid by a glue layer, a rivet, or the like, or a combination thereof. However, those variations and modifications do not depart the scope of the present disclosure.

Figure 8:
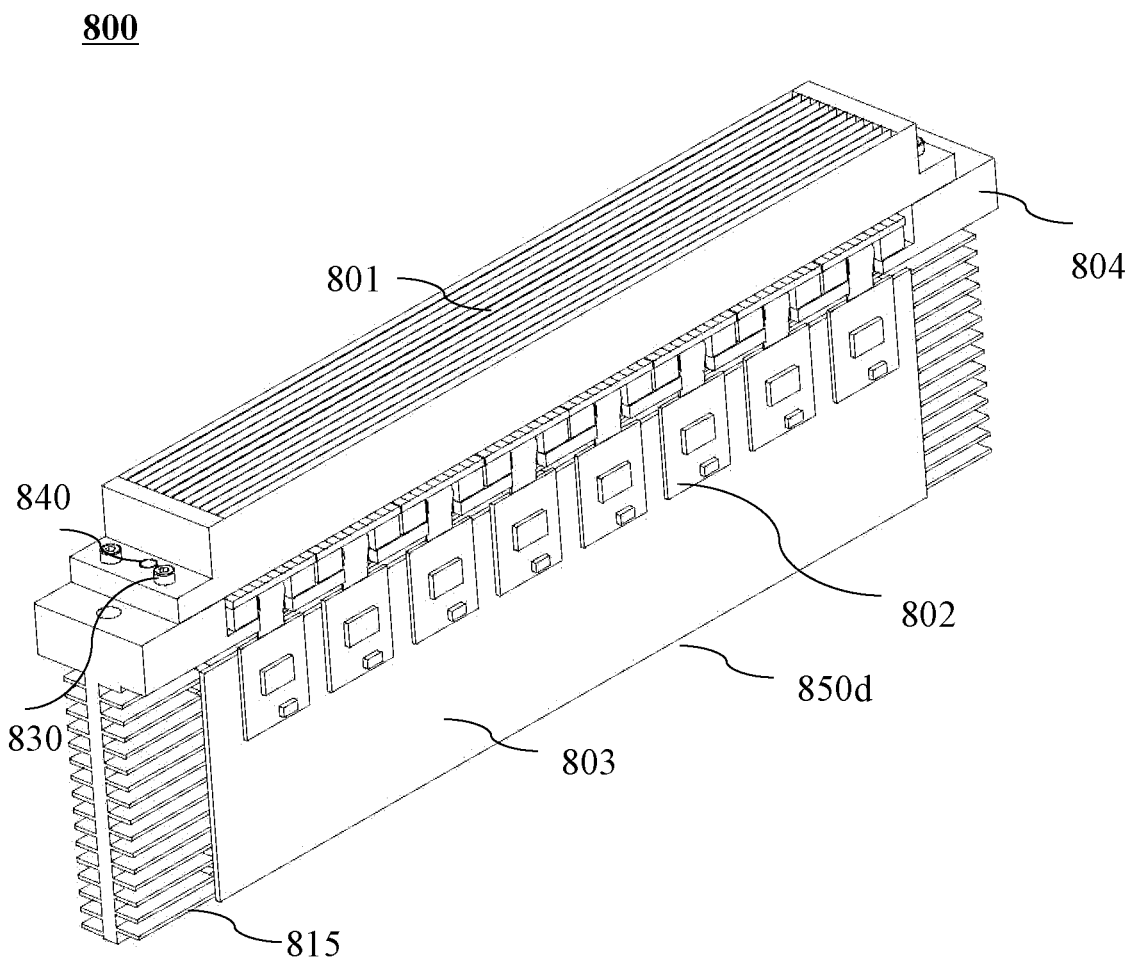
FIG. 8 illustrates a perspective view of an exemplary detector module according to some embodiments of the present disclosure.

FIG. 8 illustrates a perspective view of an exemplary detector module 800 according to some embodiments of the present disclosure. As shown, the detector module 800 may include an anti-scatter grid 801, an alignment pin 840, a plurality of threaded fasteners 830, and a detector sub-module 850d. The detector sub-module 850d may include a frame 804, a plurality of heat transfer fins 815, a plurality of signal transmission boards 802, and a data acquisition circuitry 803.

A detection layer may be electrically connected with the data acquisition circuitry 803 via the plurality of signal transmission boards 802. The alignment pin 840 and the plurality of threaded fasteners 830 may be used to assemble the anti-scatter grid 801 and the detector sub-module 850d together. The plurality of heat transfer fins 815 may be disposed on two sides of the columnar part of the frame 804. In some embodiments, the heat transfer fins may be symmetrically or asymmetrically arranged on the two sides of the columnar part of the frame 804. The number of heat transfer fins on each side of the columnar part of the frame 804 may be the same or different. In some embodiments, the data acquisition circuitry 803 may include a data acquisition circuitry that is thermally connected with the heat transfer fins 815 on one side of the columnar part of the frame 804. In some embodiments, the data acquisition circuitry 803 may include two data acquisition circuitries. The two data acquisition circuitries may be thermally connected with the heat transfer fins 815 arranged on different sides of the columnar part 804, respectively.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the detector sub-module 850*d* may be connected to the anti-scatter grid 801 by a glue layer, a rivet, or the like, or a combination thereof. However, those variations and modifications do not depart the scope of the present disclosure.

Figure 9:
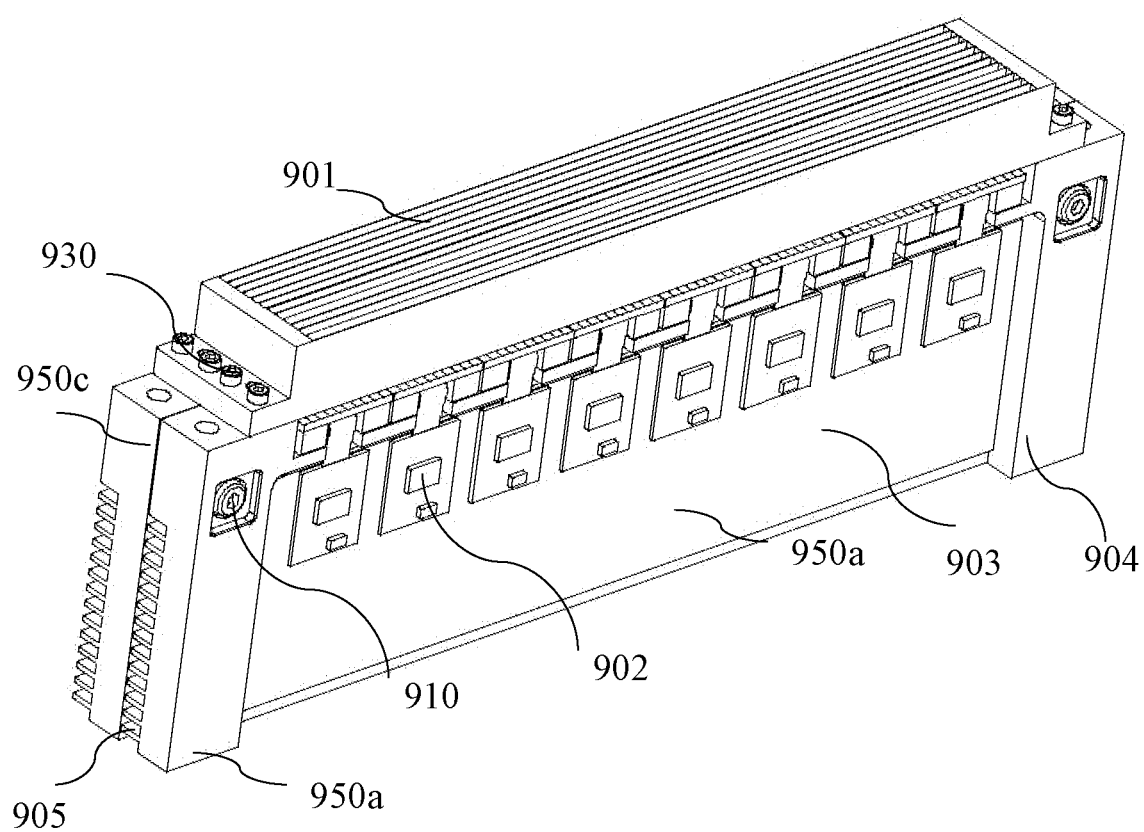
FIG. 9 illustrates a perspective view of an exemplary detector module according to some embodiments of the present disclosure.

FIG. 9 illustrates a perspective view of an exemplary detector module 900 according to some embodiments of the present disclosure. As shown, the detector module 900 may include an anti-scatter grid 901, a bolt 910, a plurality of threaded fasteners 930, a first detector sub-module 950*a*, and a second detector sub-module 950*c*. Each of the first detector sub-module 950*a* and the second detector sub-module 950*c* may include a frame 904, a plurality of heat transfer fins 905, a plurality of signal transmission boards 902, and a data acquisition circuitry 903. The plurality of heat transfer fins 905 may be located on one side of the frame 904. The anti-scatter grid 901 may be located at the top of the detector module 900. The detector module 900 may be assembled by inserting the bolt 910 through the first detector sub-module 950*a* and the second detector sub-module 950*c* and fastening the bolt by a nut. The first detector sub-module 950*a* may include a boss. The second detector sub-module 950*c* may include a recessed pocket. The recessed pocket of the second detector sub-module 950*c* may receive the boss of the first detector sub-module 950*a*. The bolt 910 may pass through both the boss and the recessed pocket. The plurality of threaded fasteners 930 may be used to assemble the anti-scatter grid 901 at the top of the first detector sub-module 950*a* and the second detector sub-module 950*c*.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the first detector sub-module 950*a* may be connected to the anti-scatter grid 901 by a glue layer, a rivet, or the like, or a combination thereof. However, those variations and modifications do not depart the scope of the present disclosure.

Figure 10:
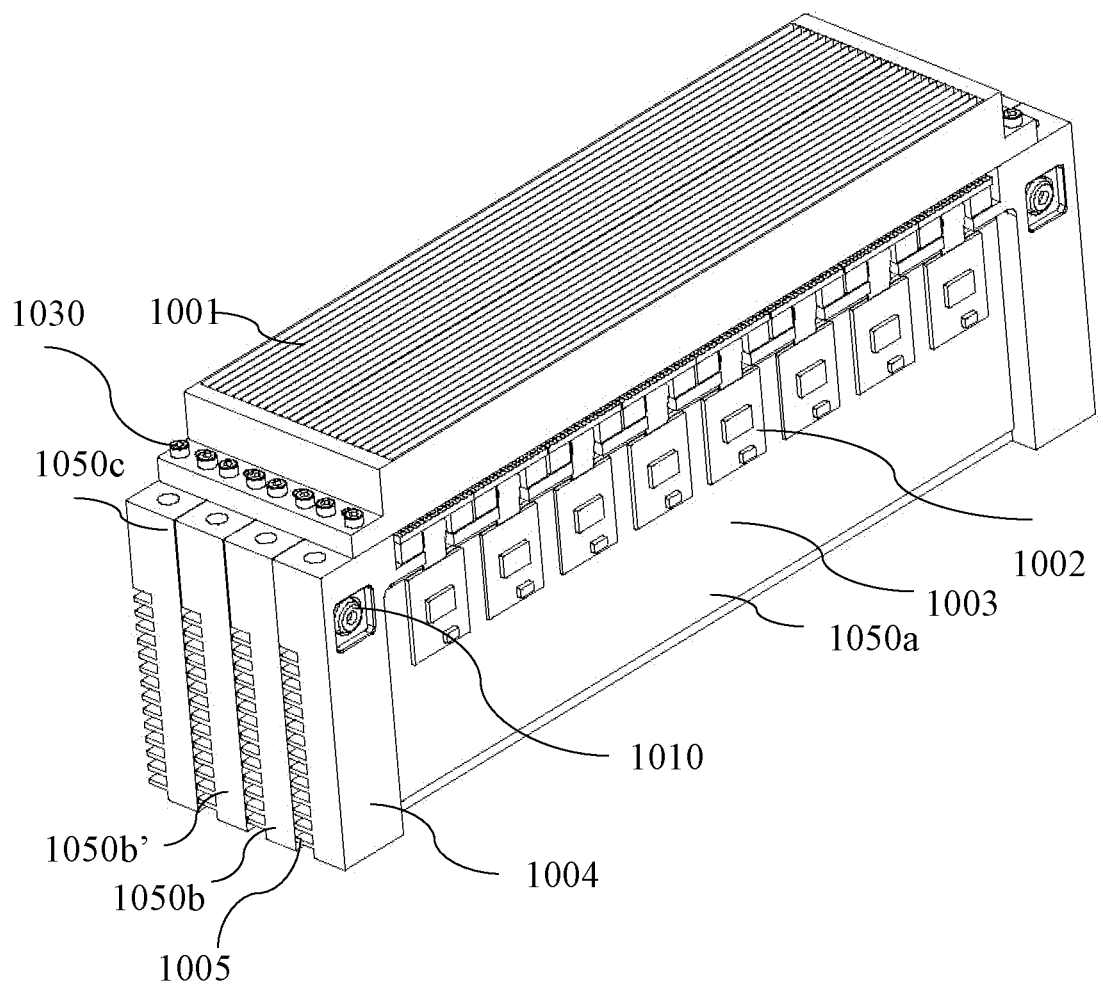
FIG. 10 illustrates a perspective view of an exemplary detector module according to some embodiments of the present disclosure.

It shall be noted that any other number of detector sub-modules may be assembled in a detector module. For example, as shown in FIG. 10, a detector module 1000 may include an anti-scatter grid 1001, a bolt 1010, a plurality of threaded fasteners 1030, a first detector sub-module 1050*a*, a second detector sub-module 1050*b*, a third detector sub-module 1050*b'*, and a fourth detector sub-module 1050*c*. Each of these detector sub-modules may include a frame 1004, a plurality of heat transfer fins 1005, a plurality of signal transmission boards 1002, and a data acquisition circuitry 1003.

Similar to the description of FIG. 9, the detector module 1000 may be assembled by inserting the bolt 1010 through the first detector sub-module 1050*a*, the second detector sub-module 1050*b*, the third detector sub-module 1050*b'*, and the fourth detector sub-module 1050*c*. A pair of adjacent detector sub-modules, such as the first detector sub-module 1050*a* and the second detector sub-module 1050*b*, may be aligned via a boss on the first detector sub-module 1050*a* received in a recessed pocket on the second detector-sub module 1050*b*. The second detector sub-module 1050*b* may further include a boss on the side facing the third detector sub-module 1050*c* such that the boss on the second detector sub-module 1050*b* may be received by the recessed pocket on the third detector sub-module 1050*c*.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the anti-scatter grid 1001 may be attached on the detector sub-modules via a glue layer, a rivet, or the like, or a combination thereof. However, those variations and modifications do not depart the scope of the present disclosure.

Figure 11A:
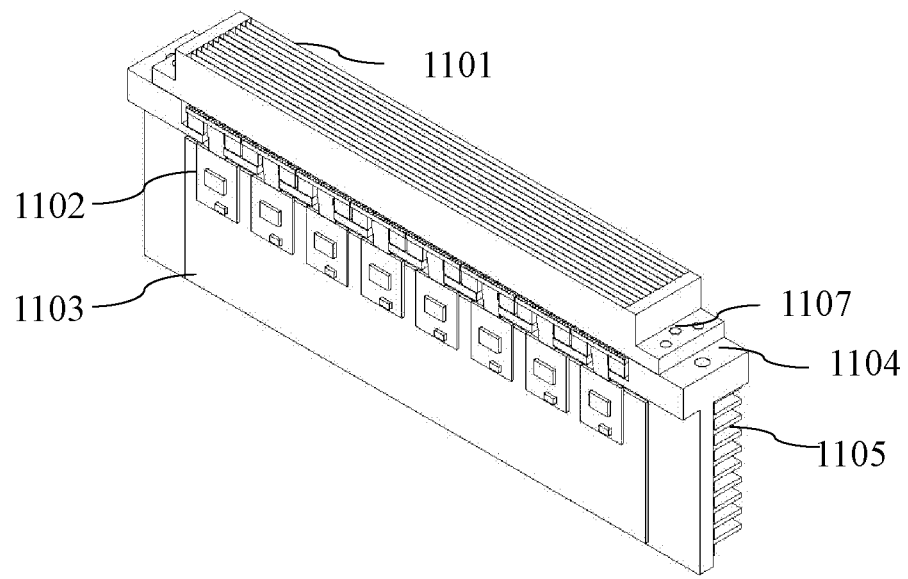
FIGS. 11A and 11B illustrate perspective views of an exemplary detector sub-module according to some embodiments of the present disclosure.
Figure 11B:
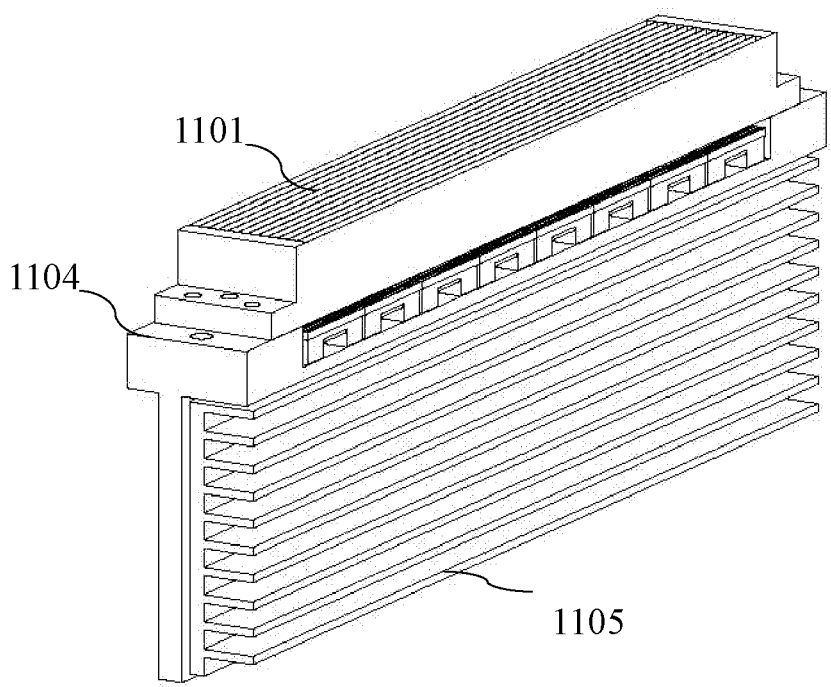

FIGS. 11A and 11B illustrate an exemplary detector sub-module 1100 according to some embodiments of the present disclosure. As shown, the detector sub-module 1100 may include an anti-scatter grid 1101, a plurality of signal transmission boards 1102, a data acquisition circuitry 1103, a frame 1104, a plurality of heat transfer fins 1105, and a pin hole 1107.

As shown, the anti-scatter grid 1101 may be disposed at the top of the frame 1104. The pin hole 1107 may be configured to facilitate the assembly of the anti-scatter grid 1101 with the frame 1104. The plurality of signal transmission boards 1102 may be disposed on the data acquisition circuitry 1103. The data acquisition circuitry 1103 may be attached to the columnar part of the frame 1104. The plurality of heat transfer fins 1105 and the data acquisition circuitry 1103 may be disposed on opposite sides of the frame 1104. Heat generated by the data acquisition circuitry 1103 may be dissipated via the heat transfer fins 1105.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the frame 1104 and the plurality of heat transfer fins 1105 may be manufactured together as a one-piece or integral component, or the plurality of heat transfer fins 1105 may be inserted into one or more slots in the frame 1104. However, those variations and modifications do not depart the scope of the present disclosure.

Figure 12A:
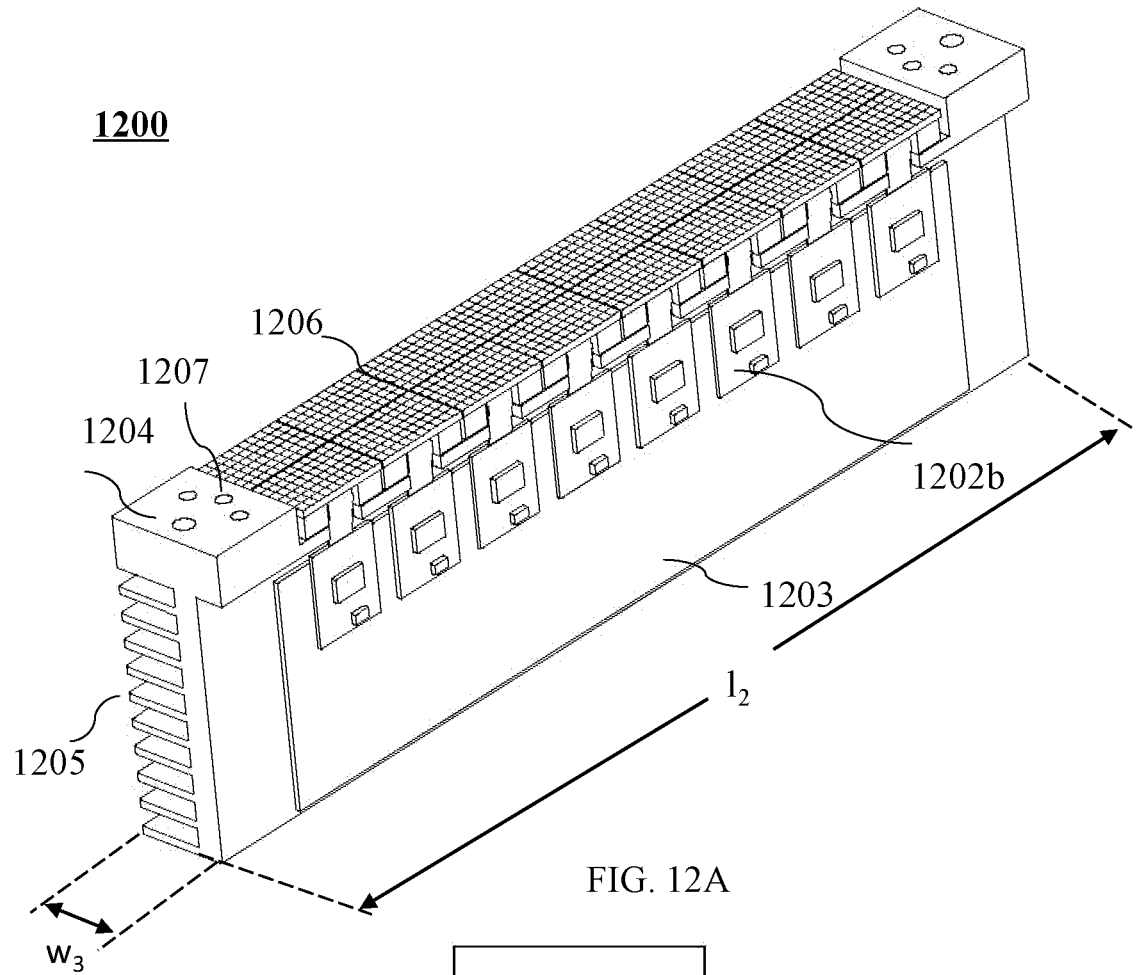
FIGS. 12A and 12B illustrate a perspective view and a side view of an exemplary detector sub-module according to some embodiments of the present disclosure.
Figure 12B:
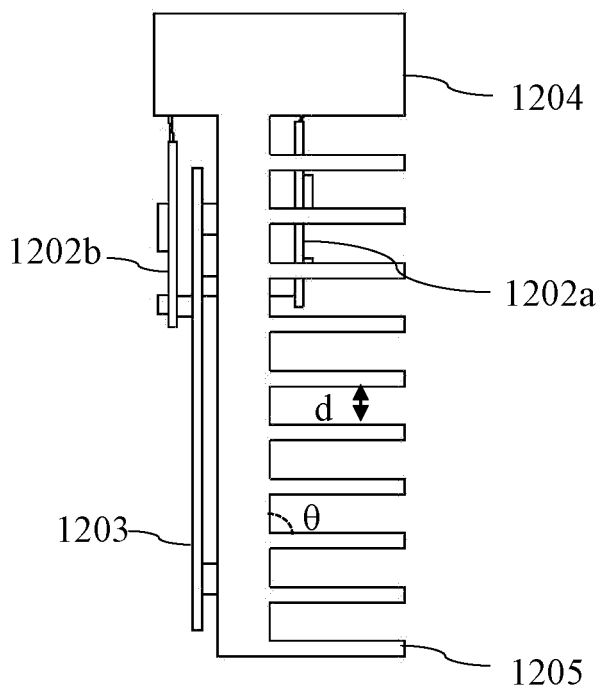

FIGS. 12A and 12B illustrate an exemplary detector sub-module 1200 according to some embodiments of the present disclosure. As shown, the detector sub-module 1200 may include a plurality of signal transmission boards 1202*a* and 1202*b*, a data acquisition circuitry 1203, a frame 1204, a plurality of heat transfer fins 1205, a detection layer 1206, and a pin hole 1207.

In some embodiments, the detection layer 1206 may be disposed at the top of the frame 1204. The detection layer 1206 may include a plurality of groups of pixels. A group of pixels may include a plurality of pixels arranged within a certain region (e.g., a rectangular region as shown in FIG. 12A). The groups of pixels may be arranged in different rows (e.g., two rows with 8 groups of pixels in each row as shown in FIG. 12A). The detection layer 1206 may be electrically connected with the plurality of signal transmission boards 1202a and 1202b. The plurality of signal transmission boards 1202a and 1202b may be electrically connected with the data acquisition circuitry 1203. The plurality of heat transfer fins 1205 and the data acquisition circuitry 1203 may be disposed on opposite sides of the frame 1204. The plurality of signal transmission boards 1202a may be thermally connected with the data acquisition circuitry 1203.

In some embodiments, the length of the plurality of heat transfer fins 1205 (i.e., $l_2$) may be the same as the length of the frame 1204. In some embodiments, the length of at least one of the plurality of heat transfer fins may be different from (e.g., shorter or longer) than the length of the frame 1204. In some embodiments, the width of the plurality of heat transfer fins 1205 (i.e., $w_3$) may be the same or different. The width $w_3$ may be configured such that the outermost edge of the fin is aligned to the edge of the frame 1204, or may be shorter.

In some embodiments, the frame 1204 and the plurality of heat transfer fins 1205 may be manufactured as a one-piece component. The plurality of heat transfer fins 1205 may be manufactured using a single material. As another example, the plurality of heat transfer fins 1205 may be manufactured as separate components made of the same material or different materials. Separate heat transfer fins 1205 may be mounted to the frame 1204 as part of an installation process.

The signal transmission board 1202a may include any suitable number of signal transmission boards. The number of signal transmission boards 1202a may be the same as or different from the number of signal transmission boards 1202b. Merely by way of example, a signal transmission board 1202a may be connected to a signal transmission board 1202b. As another example, at least two signal transmission boards 1202a may be connected to a same signal transmission board 1202b.

In some embodiments, the plurality of heat transfer fins 1205 may be parallel to each other. The angle formed by the columnar part of the frame 1204 and each of the plurality of heat transfer fins 1205 may be in a range of 45 degrees to 90 degrees. The interspace d may be of any suitable value. Merely by way of example, the interspace d between two adjacent heat transfer fins may be in the range of about 0.5 cm to about 4 cm.

FIGS. 13A and 13B illustrate an exemplary detector sub-module 1300 according to some embodiments of the present disclosure. As shown, the detector sub-module 1300 may include a plurality of signal transmission boards 1302a and 1302b, a frame 1304, a plurality of heat transfer fins 1305a and 1305b, a data acquisition circuitry 1303a, a data acquisition circuitry 1303b, and a detection layer 1306.

The detection layer 1306 may be disposed at the top of the frame 1304. The plurality of signal transmission boards 1302a and 1302b may be disposed on opposite sides of the columnar part of the frame 1304. The data acquisition circuitry 1303a and the data acquisition circuitry 1303b may be disposed on opposite sides of the columnar part of the frame 1304. The plurality of heat transfer fins 1305a and 1305b may be disposed opposite sides of the columnar part of the frame 1204. The plurality of heat transfer fins 1305b may be disposed so as to be thermally connected with the data acquisition circuitry 1303a. The data acquisition circuitry 1303a may be electrically connected with the signal transmission board 1302a. The plurality of heat transfer fins 1305a may be disposed so as to be thermally connected with the data acquisition circuitry 1303b. The data acquisition circuitry 1303b may be electrically connected with the signal transmission board 1302b.

The detection layer 1306 (not shown in FIG. 13B) may be electrically connected with the plurality of signal transmission boards 1302b. The plurality of signal transmission boards 1302b may be configured to transmit signals from the detection layer 1306 to the data acquisition circuitry 1303b. The data acquisition circuitry 1303b may be configured to process the signals received from the plurality of signal transmission boards 1302b. The processing may produce a considerable amount of heat. The plurality of heat transfer fins 1305b may be configured to dissipate the heat produced by the data acquisition circuitry 1303b.

In some embodiments, the number of the signal transmission boards 1302a may be the same as or different from the number of the signal transmission boards 1302b.

Figure 14:
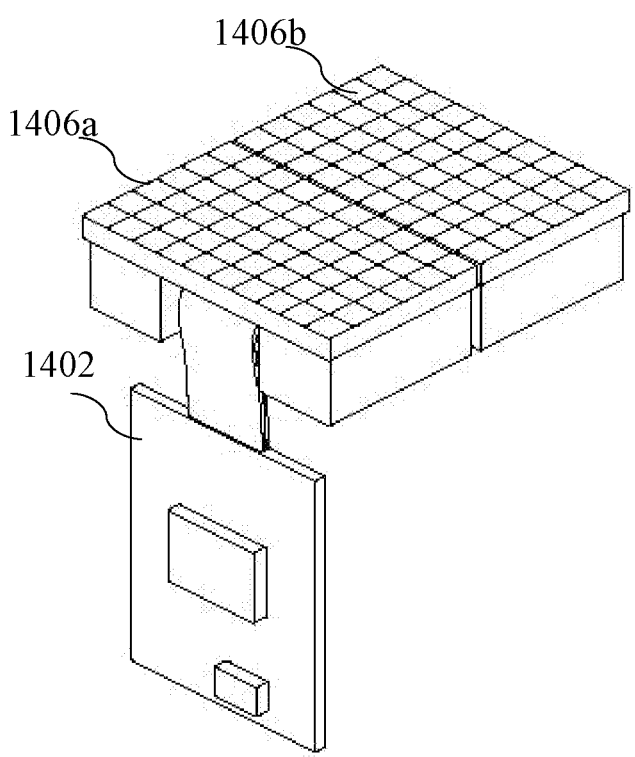
FIG. 14 is a perspective view of a detection unit according to some embodiments of the present disclosure.

FIG. 14 is a perspective view of a portion of a detection layer connecting to a signal transmission board according to some embodiments of the present disclosure. As shown, each of two groups of pixels 1406a and 1406b may present a matrix form of pixels. The two groups of pixels 1406a and 1406b may be electrically connected with a same signal transmission board 1402. The signal transmission board 1402 may be further connected to a data acquisition circuitry to process the data acquired through the two groups of pixels 1406a and 1406b.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, three or more groups of pixels may be connected to a same signal transmission board. However, those variations and modifications do not depart the scope of the present disclosure.

It should be noted that the above description of the embodiments are provided for the purposes of comprehending the present disclosure, and not intended to limit the scope of the present disclosure. For persons having ordinary skills in the art, various variations and modifications may be conducted in the light of the present disclosure. However, those variations and the modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "block," "module," "engine," "unit," "component," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a frame wave. Such a propagated signal may take any of a variety of forms, including electromagnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object-oriented programming language such as Java, Scala, Smalltalk, Eiffel, JADE, Emerald, C++, C#, VB. NET, Python or the like, conventional procedural programming languages, such as the "C" programming language, Visual Basic, Fortran 2008, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution—e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities of ingredients, properties, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and describe.

What is claimed is:

1. A detector module comprising:
a plurality of detector sub-modules including a first detector sub-module and a second detector sub-module adjacent to the first detector sub-module, the plurality of detector sub-modules being detachably assembled, wherein the first detector sub-module comprises a first positioning element, and the second detector sub-module comprises a second positioning element, wherein each of the plurality of detector sub-modules comprises: a detection layer configured to detect radiation; at least one data acquisition circuitry electrically connected with the detection layer, the at least one data acquisition circuitry being configured to process an electrical signal in response to the radiation detected by the detection layer; a frame for supporting the detection layer and the at least one data acquisition circuitry; and wherein the first positioning element includes a boss, the second positioning element includes a recessed pocket, and the first positioning element and the second positioning element form a mating connection in which the second positioning element receives the first positioning element.

2. The detector module of claim 1, wherein the first positioning element of the first detector sub-module is disposed on a first side of the first detector sub-module, the second positioning element of the second detector sub-module is disposed on a second side of the second detector sub-module, and the second side of the second detector sub-module is situated to face the first side of the first detector sub-module.

3. The detector module of claim 2, wherein the plurality of detector sub-modules are assembled based on a bolt inserted through the boss and the recessed pocket.

4. The detector module of claim 1, wherein a detector sub-module of the plurality of detector sub-modules further comprises a plurality of fins thermally connected with the at least one data acquisition circuitry of the detector sub-module.

5. The detector module of claim 4, wherein the plurality of fins of the detector sub-module are disposed on a first side of the frame, and the data acquisition circuitry is disposed on a second side of the frame, the second side of the frame being opposite to the first side of the frame.

6. The detector module of claim 5, wherein the at least one data acquisition circuitry is electrically connected with two signal transmission boards disposed on opposite sides of the frame, and the two signal transmission boards are electrically connected to the detection layer of the detector sub-module.

7. The detector module of claim 5, wherein the at least one data acquisition circuitry is electrically connected with a signal transmission board disposed on a same side of the frame as the at least one data acquisition circuitry.

8. The detector module of claim 4, wherein the plurality of fins are disposed on opposite sides of the frame.

9. The detector module of claim 8, wherein the detector sub-module comprises two data acquisition circuitries disposed on opposite sides of the frame of the detector sub-module.

10. The detector module of claim 9, wherein the detector sub-module comprises two signal transmission boards disposed on opposite sides of the frame, each of the two signal transmission boards is electrically connected with one of the two data acquisition circuitries.

11. The detector module of claim 1, wherein the frame is configured to support an anti-scatter grid disposed on a top of the detection layer.

12. A detector module, comprising:
a frame; a detection layer supported by the frame and configured to detect radiation; at least one data acquisition circuitry electrically connected with the detection layer, the at least one data acquisition circuitry being configured to process an electrical signal in response to the radiation detected by the detection layer; and a heat dissipation structure coupled to the frame, wherein the heat dissipation structure comprises a plurality of fins thermally coupled with the at least one data acquisition circuitry, wherein the plurality of fins are disposed on a first side of the frame, and the at least one data acquisition circuitry is disposed on a second side of the frame, the first side being opposite to the second side.

13. The detector module of claim 12, wherein the at least one data acquisition circuitry is electrically connected with a first signal transmission board disposed on a same side of the frame as the at least one data acquisition circuitry, and the first signal transmission board is electrically connected to the detection layer of the detector module.

14. The detector module of claim 13, wherein the at least one data acquisition circuitry is electrically connected with a second signal transmission board disposed on a same side of the frame as the plurality of fins, and the second signal transmission board is electrically connected to the detection layer of the detector module.

15. The detector module of claim 12, wherein a first portion of the plurality of fins are disposed on a third side of the frame, a second portion of the plurality of fins are disposed on a fourth side of the frame, and the third side is opposite to the fourth side.

16. The detector module of claim 15, wherein the at least one data acquisition circuitry is disposed on the third side or the fourth side of the frame.

17. The detector module of claim 15, wherein the at least one data acquisition circuitry comprises a first data acquisition circuitry and a second data acquisition circuitry, the first data acquisition circuitry is disposed on the third side of the frame, and the second data acquisition circuitry is disposed on the fourth side of the frame.

18. The detector module of claim 17, wherein the first data acquisition circuitry is electrically connected with a third signal transmission board disposed on a same side of the frame as the first data acquisition circuitry, and the second data acquisition circuitry is electrically connected with a fourth signal transmission board disposed on a same side of the frame as the second data acquisition circuitry.

19. The detector module of claim 12, further comprising:
a recessed pocket disposed on the frame, wherein the recessed pocket is configured to receive a boss of another detector module to assemble the detector module and the other detector module.

* * * * *